United States Patent
Baker et al.

(10) Patent No.: US 11,634,676 B2
(45) Date of Patent: Apr. 25, 2023

(54) INTRACELLULAR DELIVERY USING MICROFLUIDICS-ASSISTED CELL SCREENING (MACS)

(71) Applicant: PRESIDENT AND FELLOWS OF HARVARD COLLEGE, Cambridge, MA (US)

(72) Inventors: Charles James Baker, Cambridge, MA (US); Ghee Chuan Lai, Cambridge, MA (US); Dirk Landgraf, Cambridge, MA (US); Burak Okumus, Cambridge, MA (US); Johan Paulsson, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 560 days.

(21) Appl. No.: 16/631,532

(22) PCT Filed: Jul. 18, 2018

(86) PCT No.: PCT/US2018/042638
§ 371 (c)(1),
(2) Date: Jan. 16, 2020

(87) PCT Pub. No.: WO2019/018497
PCT Pub. Date: Jan. 24, 2019

(65) Prior Publication Data
US 2020/0172845 A1    Jun. 4, 2020

Related U.S. Application Data

(60) Provisional application No. 62/533,801, filed on Jul. 18, 2017.

(51) Int. Cl.
C12M 3/06 (2006.01)
B01L 3/00 (2006.01)
C12M 1/42 (2006.01)

(52) U.S. Cl.
CPC ....... *C12M 23/16* (2013.01); *B01L 3/502776* (2013.01); *C12M 35/04* (2013.01); *B01L 2200/027* (2013.01); *B01L 2400/082* (2013.01)

(58) Field of Classification Search
CPC . C12M 23/16; C12M 35/04; B01L 3/502776; B01L 2200/027; B01L 2400/082
See application file for complete search history.

(56) References Cited

U.S. PATENT DOCUMENTS

2002/0145231 A1* 10/2002 Quake ................ F16K 99/0046
264/267
2010/0297108 A1  11/2010 Henco et al.
(Continued)

FOREIGN PATENT DOCUMENTS

WO    2015/162170 A1    10/2015
WO    2016/070136 A1    5/2016
(Continued)

OTHER PUBLICATIONS

Okumus et al. "Mechanical slowing-down of cytoplasmic diffusion allows in vivo counting of proteins in individual cells." Nature Communications 7(11641):1-10(2016) (Year: 2016).*
(Continued)

*Primary Examiner* — Michael L Hobbs
(74) *Attorney, Agent, or Firm* — Nixon Peabody LLP; David S. Resnick; Jeanne Jodoin

(57) ABSTRACT

Described herein are methods inducing the uptake of an agent by a cell. Aspects of the invention relate to physically compressing the cell to induce perturbations (e.g., holes) in
(Continued)

the cell membrane or wall. An agent is taken up by the cell through induced perturbations.

19 Claims, 9 Drawing Sheets

(56) References Cited

U.S. PATENT DOCUMENTS

2015/0197755 A1   7/2015  Duan
2017/0159017 A1   6/2017  Liu et al.

FOREIGN PATENT DOCUMENTS

WO    WO-2016070136 A1 *  5/2016  ............. A61K 39/00
WO    2016/109864 A1  7/2016

OTHER PUBLICATIONS

Barakat et al. "BA10: Squeezing of vesicle through narrow tubes," The Society of Rheology 88th Annual Meeting Booklet—p. 19(2017)Internet:www.rheology.org/sor/publications/Meeting_Booklets/SoR_Abst_172.pdf>on Aug. 30, 2018).

Fedosov et al., "A multiscale red blood cell model with accurate mechanics, rheology, and dynamics." Biophysical Journal 98(10):2215-2225 (2010).

Greenberg et al., "Phagocytosis and innate immunity." Current Opinion in Immunology 14(1):136-145 (2002).

Okumus et al., "Mechanical slowing-down of cytoplasmic diffusion allows in vivo counting of proteins in individual cells." Nature Communications 7(11641):1-10 (2016).

* cited by examiner

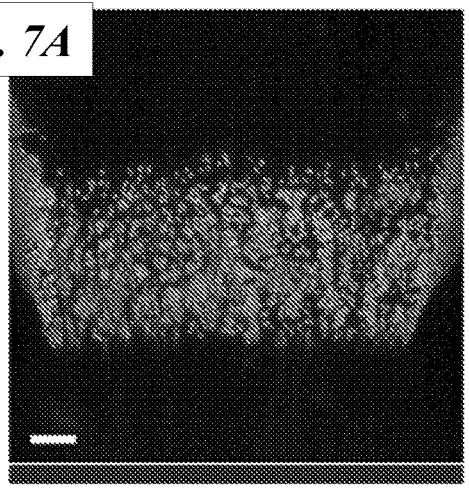
FIG. 7A
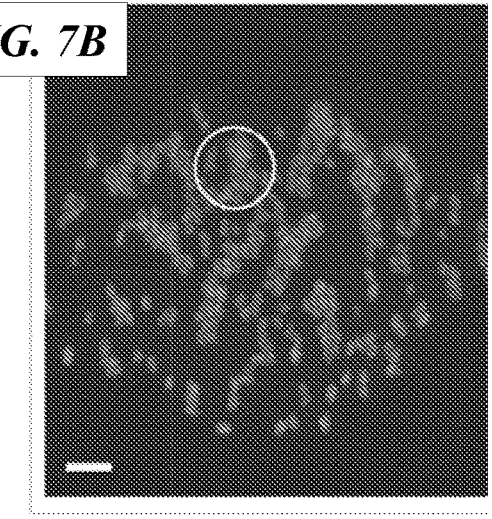
FIG. 7B
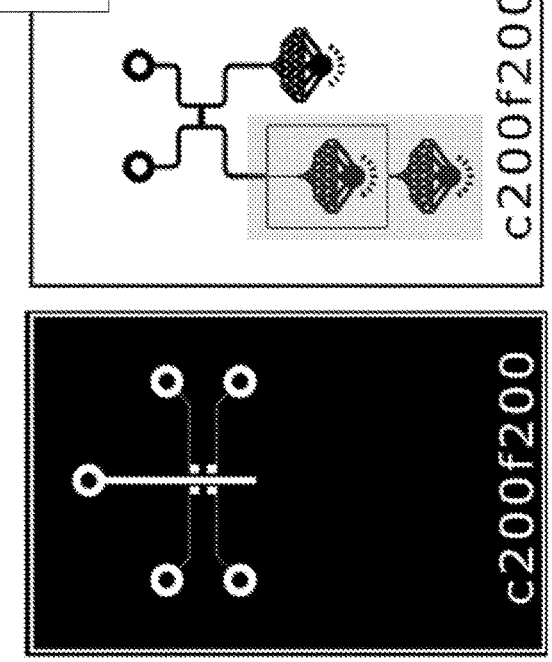
FIG. 7C
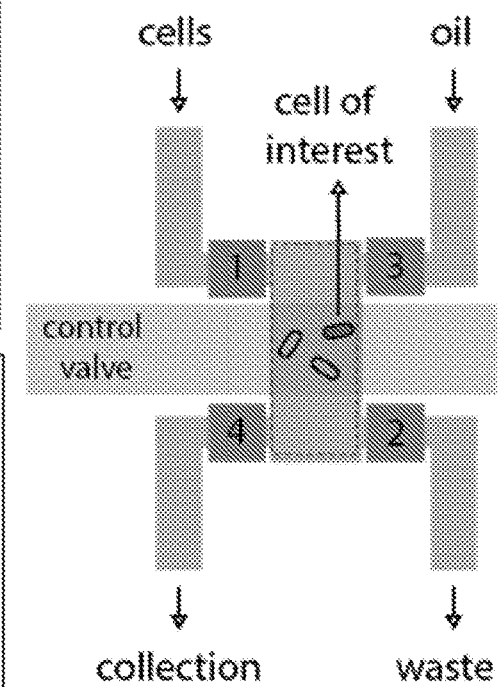

INTRACELLULAR DELIVERY USING MICROFLUIDICS-ASSISTED CELL SCREENING (MACS)

CROSS-REFERENCE TO RELATED APPLICATIONS

The present application is a 35 U.S.C. § 371 National Phase Entry Application of International Application No. PCT/US18/042638 filed Jul. 18, 2018, which designates the U.S. and claims benefit under 35 U.S.C. § 119(e) of the U.S. Provisional Application No. 62/533,801 filed Jul. 18, 2017, the contents of which are incorporated herein by reference in its entirety.

GOVERNMENT SUPPORT

This invention was made with government support under GM081563 and GM009578 awarded by the National Institutes of Health (NIH). The government has certain rights in this invention.

FIELD OF THE INVENTION

The field of the invention relates to methods promoting cellular uptake of an agent by microfluidics-assisted cell screening (MACS)-induced cell compression.

BACKGROUND

The capacity to deliver small molecule, protein, DNA or RNA based therapies is hindered by the inability for these reagents to readily cross the cellular membrane and thus require cellular modification to facilitate delivery. An efficient method for intracellular delivery is a critical step in the research, development and implementation of small molecule, protein, DNA or RNA based therapies. Established methods, for example chemicals or electrical pulses to breach the membrane and deliver the material into the cytoplasm, have draw backs and effect cell viability. Existing methods are often difficult to modify and highly specific to their particular application. Moreover, many clinically important cell types, such as stem cells and immune cells, are not properly addressed by existing methods. There is thus a need for more robust and precise technique capable of addressing the needs of modern biological and medical research.

SUMMARY

The methods disclosed herein are based, in part, on the discovery that MACS is useful in promoting cellular uptake of an agent present in the media in which cells are suspended in. Accordingly, one aspect of the invention described herein relates to a method for uptake of an agent into a cell or population thereof using a microfluidic device by passing a first flow fluid through a flow channel of the microfluidic device, the flow channel being at least partially bounded on a first side by a flexible layer of the microfluidic device and being at least partially bounded on an opposing second side by a rigid layer of the microfluidic device, the first flow fluid including a plurality of a first type of cell therein and a first agent; pressurizing a control channel formed in the flexible layer of the microfluidic device such that the flexible layer physically compresses at least one of the first type of cell in the first flow fluid against the rigid layer to induce at least one temporary perturbation in a membrane of the at least one of the first type of cell; and causing a portion of the first agent to be taken up by the at least one of the first type of cell through the at least one temporary perturbation in the membrane of the at least one of the first type of cell.

in some embodiments, the aspect further comprises passing a second flow fluid through the flow channel of the microfluidic device, the second flow fluid including a plurality of a second type of cell therein that is different from the first type of cell and a second agent; pressurizing the control channel formed in the flexible layer of the microfluidic device such that the flexible layer physically compresses at least one of the second type of cell in the second flow fluid against the rigid layer to induce at least one temporary perturbation in a membrane of the at least one of the second type of cell; and causing a portion of the second agent to be taken up by the at least one of the second type of cell through the at least one temporary perturbation in the membrane of the at least one of the second type of cell.

In some embodments, the method further comprises manually adjusting the rate of compression between the flowing the first and second type of cell or population thereof.

In some embodments of aspects described herein, a first and second agent is taken up by the first and second type of cell or population thereof.

In some embodments, causing the portion of the first and second agent to be taken up includes continuing to flow the fluid through the flow channel with the control channel pressurized.

In other embodiments, causing the portion of the first and second agent to be taken up includes adjusting a flow rate of the fluid through the flow channel with the control channel pressurized.

In another embodiment, causing the portion of the first and second agent to be taken up includes stopping the flow of the fluid through the flow channel with the control channel pressurized.

In some embodiments, the first and second agent are not cell permeable.

In one embodiment, the first and second agent are the same.

In one embodiment, the first and second agent are different.

Non-limiting examples of an agent include a DNA-staining dye, a fluorescent molecule, a plasmid, a vector, a protein, a nucleic acid, a polypeptide, recombinant DNA, RNA, siRNA, shRNA, miRNA, a compound, a small molecule, an antibody, a virus, a quantum dot (Qdot), a chromosome, a nuclei acid that encodes receptors for CAR T-cells, a drug, a therapeutic, an anti-sense oligonucleotide (ASO), an mRNA, an RNA aptamer, a protein aggregate, a protein fibril, a nanoparticle, a polysaccharide, a lipid, an organelle, a mitochondrion, a prokaryote, a microbial cell, and a bacterial cell.

In some embodiments, the first and second flow fluid that flows through the fluid channel comprises cells and an agent. In one embodiment, the first and second flow fluid further comprises an extracellular growth factor.

In one embodiments of aspects described herein, the first and second cell type are different.

In one embodiment, the first type of cell is a prokaryotic cell and the second type of cell is a eukaryotic cell.

In one embodiment, the first type of cell and the second type of cell are different eukaryotic cells.

In one embodiment, the first type of cell and the second type of cell are different prokaryotic cells.

In one embodiment, the first type of cell and the second type of cell are different diameters.

In one embodiment, the first type of cell and the second type of cell are different shapes.

Non-limiting examples of cell types include a prokaryote, a microbial cell, a bacterial cell, a yeast cell, an artificial cell, liposome, a generally rod shape with a diameter that is less than two micrometer and a length that is less than ten micrometers, a generally rod shape with a diameter that is between about 0.2 micrometers and about two micrometer, a eukaryotic cell, a mammalian cell, an oocyte, a red blood cell, a white blood cell, a human cell, has a generally biconcave shape with a diameter that is between about two micrometers and about twenty micrometers, and has a diameter that is between about one micrometers and about twenty micrometers.

One aspect described herein relates to methods to for using a microfluidic device comprising flowing a first flow fluid through a flow channel of the microfluidic device, the flow channel being at least partially bounded on a first side by a flexible layer of the microfluidic device and being at least partially bounded on an opposing second side by a rigid layer of the microfluidic device, the first flow fluid including a plurality of a first type of cells therein and a first agent; pressurizing, to a first pressure, a control channel formed in the flexible layer of the microfluidic device such that the flexible layer physically compresses at least one of the first type of cells in the first flow fluid against the rigid layer to induce at least one temporary perturbation in a membrane of the at least one of the first type of cell and permitting the at least one of the first type of cell to take up a portion of the first agent therethrough; passing a second flow fluid through the flow channel of the microfluidic device, the second flow fluid including a plurality of a second type of cells therein that is different from the first type of cells and a second agent; and pressurizing, to a second pressure that is different from the first pressure, the control channel formed in the flexible layer of the microfluidic device such that the flexible layer physically compresses at least one of the second type of cells in the second flow fluid against the rigid layer to induce at least one temporary perturbation in a membrane of the at least one of the second type of cells and permitting the at least one of the second type of cells to take up a portion of the second agent there through.

In one embodiment, the first flow fluid is passed through the flow channel at a first time point.

In another embodiment, the second flow fluid is passed through the flow channel at a second time point.

In yet another embodiment, the second time point is a least 0.1 seconds after the first time point.

One aspect described herein relates the method comprising passing a fluid through a flow channel of a microfluidic device, the flow channel being formed by a flexible layer and a cover layer, the flexible layer including a control channel therein that extends generally perpendicular to the flow channel, the fluid including an agent and a plurality of cells therein; and pressurizing the control channel such that (i) a constriction is formed in the flow channel, and (ii) at least one of the plurality of cells in the fluid is physically compressed between the flexible layer and the cover layer at the formed constriction to induce at least one temporary perturbation in a membrane of the one of the plurality of cells and permitting the at least one of the plurality of cells to take up a portion of the agent therethrough.

In one embodiment, the method further comprises adjusting a flow rate of the fluid in the flow channel.

In another embodiment, the adjusting includes adjusting the flow rate of the fluid in the flow channel to zero flow.

Another aspect described herein relates the method comprising passing a fluid through a flow channel of a microfluidic device, the flow channel being formed by a flexible layer and a cover layer, the flexible layer including a control channel therein that extends generally perpendicular to the flow channel, the fluid including an agent and a plurality of cells therein; pressurizing the control channel; forming a constriction in the flow channel; physically compressing at least one of the plurality of cells in the fluid between the flexible layer and the cover layer at the formed constriction; inducing at least one temporary perturbation in a membrane of the at least one of the plurality of cells; and causing the at least one of the plurality of cells to take up a portion of the agent through the at least one temporary perturbation of the membrane.

In one embodiment, manually pressurizing the control channel causes the compression to occur.

In another embodiment, manually pressurizing the control channel causes the at least one of the plurality of cells to be physically compressed.

In yet another embodiment, the physical compression of the at least one of the plurality of cells induces at least one temporary perturbation in the membrane of the at least one of the plurality of cells.

In one embodiment, a pressure differential between a pressure inside the at least one of the plurality of cells and a pressure of the flow fluid causes the at least one of the plurality of cells to take up the portion of the agent through the at least one temporary perturbation of the membrane, In another embodiment of the aspect described herein, prior to the at least one of the plurality of cells being physically compressed, a pressure differential between a pressure inside the at least one of the plurality of cells and a pressure of the flow fluid is insufficient to cause the at least one of the plurality of cells to take up the portion of the agent.

Definitions

"Physical compression" and "compression" refer to the application of inward pushing forces exerted on a cell to reduce its size or deform the cell, and are used interchangeably herein. Compression is a product of pressurizing the control channel. Compression reduces the cell size by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more compared to the size of the cell prior to compression.

"Flow fluid" is any physiologic or cell-compatible buffer or solution. For example, a flow fluid is cell culture media or phosphate-buffered saline. Flow fluid can also comprise the agent intended to be taken up by the cell.

With regard to cells, the term "isolated" means that the cell is substantially free of other cell types or cellular material with which it naturally occurs. For example, a sample of cells of a particular tissue type or phenotype is "substantially pure" when it is at least 60% of the cell population. The preparation is at least 75%, at least 90%, and at least 99% or 100%, of the cell population. Purity is measured by any appropriate standard method, for example, by flow cytometry or fluorescence-activated cell sorting (FACS).

With regard to an agent, an "isolated" "purified" small molecule, nucleic acid molecule. polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. The preparation is at least 75%, at least 90%, or at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by mass spectrometry, column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Examples of a an isolated or purified nucleic acid molecule include: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones.

As used herein, a "perturbation" in the cell membrane or wall is a breach in the cell that allows material from outside the cell to move into the cell (e.g., a hole, tear, cavity, aperture, pore, break, gap, perforation).

The term "optional" or "optionally" means that the subsequent described event, circumstance or substituent may or may not occur, and that the description includes instances where the event or circumstance occurs and instances where it does not.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. The term permits the presence of elements that do not materially affect the basic and novel or functional characteristic(s) of that embodiment of the invention.

BRIEF DESCRIPTION OF THE DRAWINGS

(FIG. 1A) MACS works by serially visiting three states of the valve. Once Pcontrol and Pflow are set, three valve configurations can be achieved only by combinations of on and off states of Pcontrol and Pflow, which is controlled by the attached solenoid valves. (FIG. 1B) By using higher pressure or stiffer chips, MACS allows mechanical slowing down of diffusion, hence the visualization of single cytoplasmic molecules as small as individual proteins.

(FIG. 5A) Schematics summarizing photolithography, device making and bonding. After the control layer is prepared (left), it is aligned and bonded onto the flow channel (middle). After the two layers adhere, the two-layer PDIS chip is bonded to a cover glass (right). (FIG. 5B) Transparency masks for flow (left) and control (right) layers. The inset shows the inlet filters in more detail. (FIG. 5C) Cut through at the inlets after hole punching. (Top) Without isopropanol treatment, there are PDMS crumbs stuck to the channel (marked with a red arrow). (Bottom) After isopropanol treatment, the debris is removed from the inlet holes.

FIGS. 7A-7E shows the capturing of rare phenotypes and their retrieval using MACS. (FIG. 7A) Cells continuously flowing through the FOV in the half-open state. Scale bar (white), 25 μm. (FIG. 7B) The cell of interest an RFP-expressing cell, which are diluted by a factor of 100,000 using GFP-expressing cells—is captured in the closed state and is detected (circled). Scale bar (white), 10 μm. (FIG. 7C) Minor modification of MACS enables cell retrieval. Left. Masks for flow (top) and control (bottom) layers. The flow-focusing feature is shown within the semi-transparent gray box. This feature is optional, and allows for the cells to trickle through the central region of the flow channel and prevent cell accumulation at the channel sides. It also allows for adjusting the cell density on the FOV: when the side streams (of media) are stronger, the middle stream gets thinner, thereby diluting the cells at the FOV. Right. Schematics of cell retrieval. The volume that is trapped when valves 1-4 are closed (with the control valve open) is shown by the red dashed line. (FIG. 7D) Circled is the captured cell of interest in FIG. 4b within the trapped volume, which is outlined by the red dashed line. Shown is bright field and RFP fluorescence images overlaid. Scale bar (white) is 40 pan, (FIG. 7E) When the trapped volume using the oil phase is collected, grew cells overnight: and imaged them on the agar pad; the RFP-expressing cells were enriched. This scheme allows for the immediate retrieval of cells at low cell densities. At high densities, a second round is necessary to achieve 100% purity. Scale bar (white), 2 μm.

DETAILED DESCRIPTION

Figure 1A:
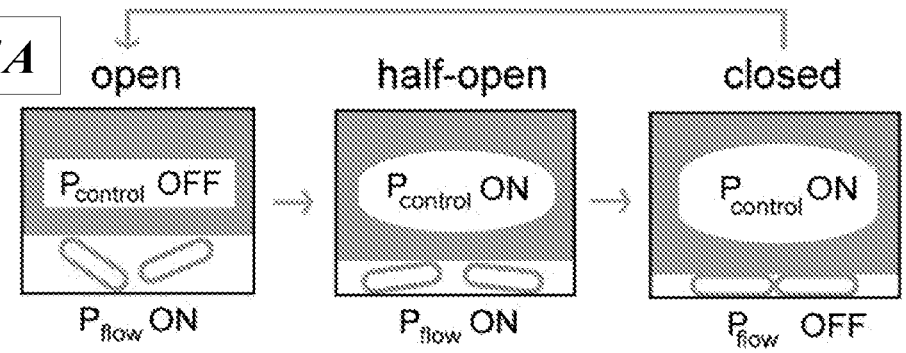
FIGS. 1A and 1B show the operating principle of MACS.

Embodiments of the invention provide techniques for applying controlled deformation to a cell for a predetermined amount of time in order to cause perturbation in the cell membrane such that or biological materials (e.g., agents) can be delivered to the inside of the cell. The deformation can be caused by, for example, pressure induced by physical compression. In one example, a microfluidic system (MACS) includes a structure that controls and/or manipulates fluids by geometrically confining the fluids on a small scale (e.g., sub milliliter-volumes such as microlitres, nanoliters, picoliters). The microfluidic system is capable of intracellularly delivering virtually any agent into a cell, for example, a small molecule, an antibody, or nuclei acid. The system consists of one or more microfluidic channels with a constriction that the cells pass through; the flow channel, which the cells pass through, and the control channel, which is manually pressurized to physically compress the flow channel. The cells flow through the microfluidic flow channel suspended in a liquid medium, referred to herein as "flow fluid" that is pressure driven through the system. When a cell is compressed, its membrane is disrupted causing temporary perturbations in the membrane that allow for an agent to pass through the membrane and resulting in the uptake of the agent that is present in the flow fluid. The rate of compression is a function of the size of the target cell, but on the same order or smaller than the cell diameter. Following compression, cells are incubated in the flow fluid containing an agent that is to be taken up by the cell. The perturbations (e.g., pores or holes) created by the methods described herein are not formed as a result of assembly of protein subunits to form a multimeric pore structure such as that created by complement or bacterial hemolysins. Other embodiments are within the scope of the described subject matter.

Microfluidics Assisted Cell Screening (MACS)

The MACS platform, disclosed in US2015/0247790, incorporated herein by reference, enables high throughput microscopy-based screening. MACS utilizes a soft flexible polymer to trap cells flowing through a flow channel. Once trapped, the cells are imaged and then released. By repeating this process over and over again, MACS enables an increase in the number cells that can be imaged each minute and provides for detecting rare events and rare cellular phenotypes. The imaging capability has been tested on both prokaryotes and eukaryotic cells (eukaryotes have typically a many times larger cell volume than prokaryotes). MACS enables localization of single molecules in cells, MACS can also be used for analysis of cell growth rates, and can detect weak fluorescent signals. As described herein, MACS can be used to facilitate cellular uptake of an agent.

The micro fluidic platform includes a flow channel, which is bordered on one side by a cell-covering element and on an opposing side a polymer layer. The cell-covering element can include, for example, a cover slip, and the polymer layer can include, for example, a soft polymer such as PDMS. PDMS belongs to a group of polymeric organosilicon compounds that are commonly referred to as silicones. It is also called dimethicone. The shear modulus of the soft polymer, e.g., PDMS, can vary with preparation conditions, but can be less than 30 GPa, and in some implementations between 100 kPa to 3 MPa. The microfluidic platform further includes a control layer within or on top of the polymer layer that is capable of selectively exerting a force (e.g., expanding) towards the cell-covering element. The control channel can include, for example, a dead-end channel formed from the polymer layer that is running in a perpendicular direction to the flow channel. Since, in the example, the polymer layer can be formed of a soft and flexible polymer (e.g., PDMS), the control channel can be actuated by injection of water or other fluid into the control channel. The injected fluid causes an increase in pressure, which causes the flexible polymer to expand (e.g., stretch or deform). Cells such as bacteria or mammalian cells suspended in a flow fluid can travel through the flow channel. A camera or other imaging means can optionally be located such that cells traversing the flow channel are within the camera field of view when they are trapped by the control layer. The position in the flow channel for trapping, compressing, and imaging the cells is referred to as the pinch point or the camera field of view. The camera can include a microscope or other lens and a light source (e.g., darkfield, brightfield, laser, strobe, and the like) for focusing and illuminating the cells in the pinch point.

It should be understood that the control channel is for lied from the polymer layer and the cell-covering element resides between the flow channel and the camera.

In the example shown in FIG. 1A left, no pressure is applied to the control channel. The flow channel is open such that the cells flow freely in the flow channel traversing the imaging camera field. In the example shown in FIG. 1A center, the control channel is pressurized by injection of water. The polymer layer (e.g., thin PDMS membrane) can deflect to seal against the cell-covering element (e.g., coverslip) due to the flexibility of the polymer. Flow rate or the pressure applied to the flow channel can then be adjusted to a level that would be able to overcome the pressure where a seal at the pinch point is broken slightly. When this occurs the cells can start slipping between the polymer layer and the cell-covering element. These cells are physically compressed. In the example of FIG. 1A right, illustrating a closed state, flow can be stopped or reduced. The polymer layer (e.g., PDMS) collapses against the cell-covering element (e.g., coverslip) in a closed state and immobilizes the cells for subsequent imaging. New cells from the flow fluid can be introduced/trapped/compressed/imaged by repeating the cycle illustrated in FIG. 1A. In some examples, simply collapsing the PDMS membrane against the cells. (i.e., going directly from FIG. 1A left to FIG. 1A right, and skipping FIG. 1A middle), can lead to displacement of the liquid and the cells altogether resulting in no cell trapping.

Figure 2:
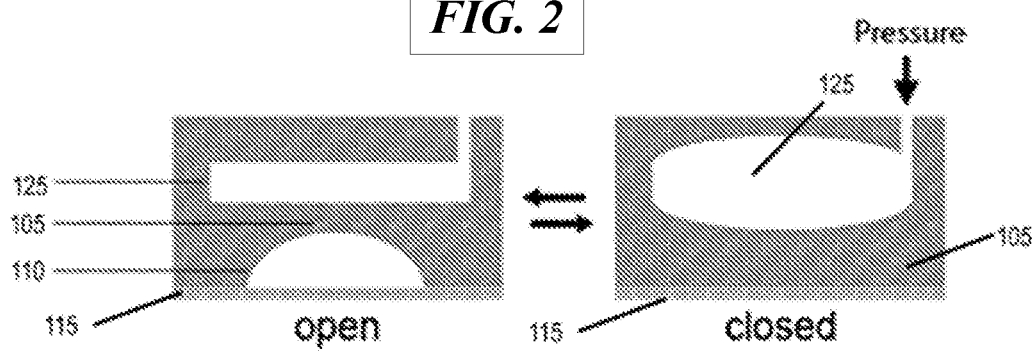
FIG. 2 series of cross section views of the example microfluidic platform.

FIG. 2 is a series of cross-section views of the example microfluidic platform illustrate(in FIG. 1A. The cross section views are at an angle perpendicular to the view illustrated in FIG. 1A (e.g., the flow of the flow channel 110 is into (or out of) the figure). In the example illustrated in FIG. 2, the flow channel 110 has a domed or curved cross section. When pressure is applied to the control channel 125, the pinch point 135 can be considered in a closed state. Thus, the microfluidic platform can operate similar to a valve, in which the flow of the fluid in the flow channel 110 is controlled.

Figure 3:
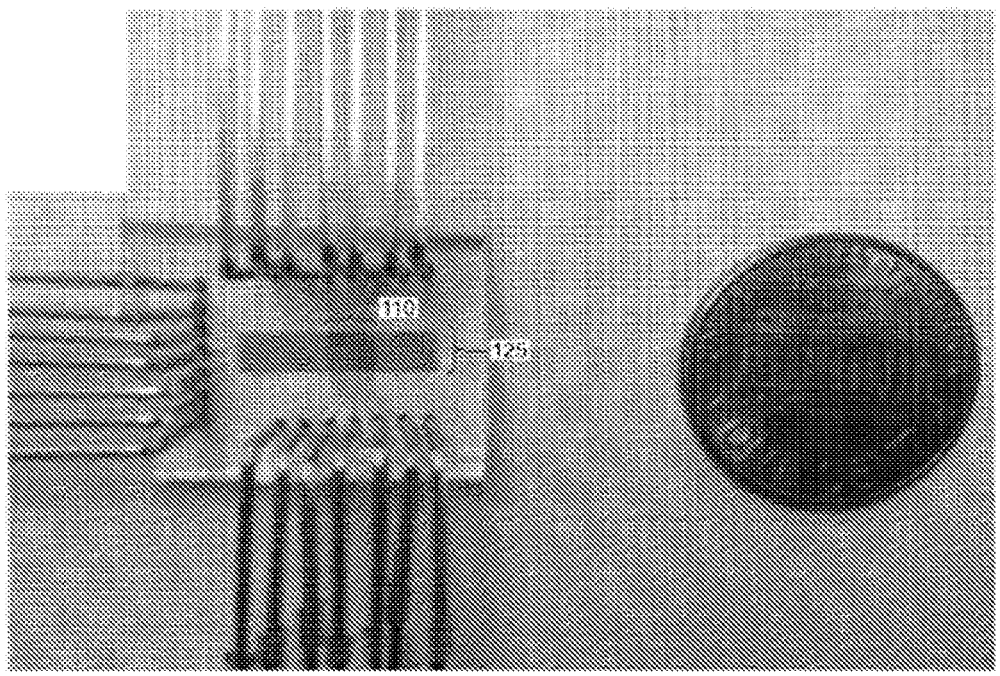
FIG. 3 is a picture illustrating the exterior of an example implementation of a microfluidic platform configured for cell screening and imaging.

FIG. 3 is a picture illustrating the exterior of an example implementation of a microfluidic platform configured for cell screening and imaging. The platform includes multiple parallel flow channels 110, which are perpendicular to multiple parallel control channels 125. The dead-end channel nature of the control channels 125 is visible. Each control channel 125 can be controlled independently (e.g., with microfluidic pumps). Similarly, the flow of each flow channel 110 can be controlled independently (e.g., with microfluidic pumps). The seven control channels 125 and seven flow channels 110 define intersections or pinch points that can be used independently. In the example implementation, both flow channels 110 and control channels 125 are 200 mm wide. Due to the small footprint of the valve it is possible to scale this up even further up-to hundreds of intersections for the uninterrupted screening of 96-well plates.

Figure 4:
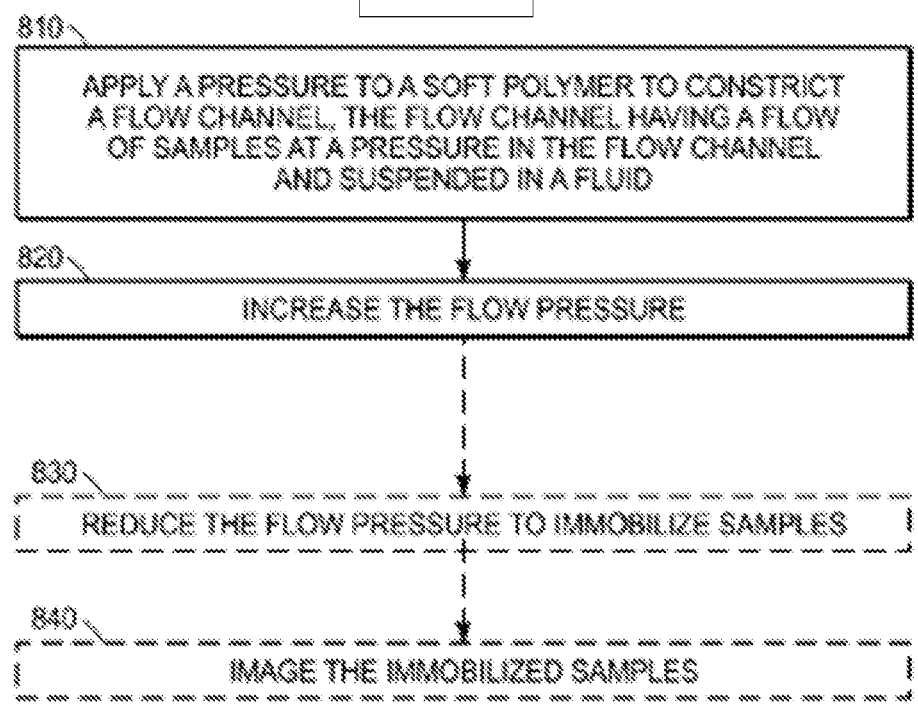
FIG. 4 is a process flow diagram for a method in accordance with the current subject matter.

FIG. 4 is a process flow diagram 800 for a method in accordance with the current subject matter. At 810, a pressure is applied to a polymer layer 105 to constrict a flow channel 110. The polymer layer 105 can form a seal with a cell-covering element 115. The flow channel 110 has a flow of samples or cells 120 suspended in fluid. The flow can be applied to the flow channel 110 at a pressure (e.g., applied by a pump). At 820, the flow pressure can be increased such that the seal is broken, allowing samples or cells to slip between the polymer layer 105 and the cell-covering element 115. Optionally, at 830, the flow pressure can be reduced (e.g., stopped, paused, or curtailed) such that some of the samples or cells are immobilized between the polymer layer 105 and cell-covering element 115. Optionally at 830, the immobilized samples or cells can be imaged by, for example, a camera with a microscope.

MACS can include a three-state valve configuration (as illustrated in, e.g., FIG. 1A left (open), FIG. 1A middle (half-open), and FIG. 1A right (closed), which enables automated, high-throughput microscopy that capitalizes on the push-down valve design. (Monolithic microfabricated valves and pumps by multilayer soft lithography. Unger M A, Chou H P, Thorsen T, Scherer A, Quake S R. Science. 2000 Apr. 7; 288(5463):113-6.) In one implementation, a screening throughput rate of 4,000 cells/minute and greater is possible. Additionally, the screening can be performed by microscopy, hence information on precise cell morphology, cell size, and accurate fluorescence intensity is readily attainable. It is also possible to obtain spatial localization of intercellular structures. The current subject matter can detect fluorescence to single-molecule detection sensitivity. By controlling the PDMS stiffness and the applied pressure, molecules can be forced to diffuse more slowly in the cytoplasm of the compressed cell. When (cytoplasmic) molecules of interest exist in very low numbers per cell, they can be directly visualized, and their abundances can accurately be quantified by direct counting fluorescent spots.

Using MACS, cells can flow continuously as a single-layer without stopping (which enables sifting through many more cells within a certain time, hence substantially higher-throughput) until a rare event of interest shows up within the field-of-view and flow may be stopped to capture the cell-of-interest such that detailed images (e.g. in different fluorescence channels) can be acquired. MACS can potentially be utilized to assay how cells respond to shear flow (compare with BioFlux by Bucher Biotec) or how cells resist applied pressures (e.g., for screening the effects of cell-wall targeting drugs). With the proper alterations, MACS can lend itself to microscopy-based cell sorting or enrichment.

The velocity at which the cells pass through the flow channel can also be varied to control delivery of the agents to the cells. For example, adjusting the velocity of the cells through the channel can vary the amount of time that compression is applied to the cells, and can vary how rapidly the compression is applied to the cell (e.g., slowly or acutely). The cells pass through the system at a rate of at least 0.1 mm/s such as 0.1 mm/s to 5 m/s, and between 10 mm/s to 500 mm/s, although other speeds are possible. In some embodiments, the cells can pass through the system at a rate greater than 5 m/s.

The cells can be driven through the flow channel by various methods. For example, pressure can be applied by a pump on the entrance side (e.g., gas cylinder, or compressor), a vacuum can be applied by a vacuum pump on the exit side, capillary action through a tube, and/or the system can be gravity fed. Displacement based flow systems can also be used (e.g., syringe pump, peristaltic pump, manual syringe or pipette, pistons. etc.). Exemplary flow rates through a single channel 10 are on the order of 1 μl in a few seconds. Additionally, flow fluid can include one or more lubricants (pluronics or other surfactants) that can be designed to reduce or eliminate clogging of the channel and improve.

The control and flow channels can be fabricated from various materials such as silicon, glass, ceramics, crystalline substrates, amorphous substrates, and polymers (e.g., Polymethyl methacrylate (PMMA), PDMS, Cyclic Olefin Copolymer (COC), etc). Fabrication is clean-room based, and can use, for example dry etching, wet etching, photolithography, injection molding, laser ablation. SU-8 masks, etc. One exemplary channel is approximately 200 μm wide, though other dimensions are possible.

An advantage of the technology described herein over other devices is the ability to manually adjust the compression rate to induce uptake of an agent into any cell type.

Manual Adjustment of Compression Rate

In one aspect of the invention, a first flow fluid is passed through a flow channel of the microfluidic device, the flow channel being at least partially bounded on a first side by a flexible layer of the microfluidic device and being at least partially bounded on an opposing second side by a rigid layer of the microfluidic device, the first flow fluid includes a plurality of a first type of cell therein and a first agent. A control channel formed in the flexible layer of the microfluidic device such that the flexible layer physically compresses at least one of the first type of cell in the first flow fluid against the rigid layer to induce at least one temporary perturbation in a membrane of the at least one of the first type of cell, causing a portion of the first agent to be taken up by the at least one of the first type of cell through the at least one temporary perturbation in the membrane of the at least one of the first type of cell. The aspect further comprises a passing a second flow fluid through a flow channel of the microfluidic device, the second flow fluid includes a plurality of a second type of cell therein and a second agent. A control channel formed in the flexible layer of the microfluidic device such that the flexible layer physically compresses at least one of the second type of cell in the second flow fluid against the rigid layer to induce at least one temporary perturbation in a membrane of the at least one of the second type of cell, causing a portion of the second agent to be taken up by the at least one of the second type of cell through the at least one temporary perturbation in the membrane of the at least one of the second type of cell.

In one embodiment, the portion of the first and second agent to be taken up includes continuing to pass the first and second flow fluid through the flow channel with the control channel pressurized. In one embodiment, the causing the portion of the first and second agent to be taken up includes adjusting a flow rate of the first and second flow fluid through the flow channel with the control channel pressurized. In another embodiment, the portion of the first and second agent to be taken up includes stopping the flow of the first and second flow fluid through the flow channel with the control channel pressurized.

In one embodiment, the second agent is the same as the first agent. In another embodiment, the second agent is different from the first agent.

In one embodiment, the first type of cell is a prokarotic cell and the second type of cell is a eukaryotic cell. In one embodiment, the first type of cell and the second type of cell are a different prokaryotic cell. In one embodiment, the first type of cell and the second type of cell are a different eukaryotic cell. In one embodiment, the first type of cell and the second type of cell are a different diameter. In one embodiment, the first type of cell and the second type of cell are a different shape.

In another aspect of the invention, a first flow fluid is passed through a flow channel of the microfluidic device, the flow channel being at least partially bounded on a first side by a flexible layer of the microfluidic device and being at least partially bounded on an opposing second side by a rigid layer of the microfluidic device, the first flow fluid including a plurality of a first type of cells therein and a first agent. A control channel is pressurized to a first pressure, a control channel formed in the flexible layer of the microfluidic device such that the flexible layer physically compresses at least one of the first type of cells in the first flow fluid against the rigid layer to induce at least one temporary perturbation in a membrane of the at least one of the first type of cell and permitting the at least one of the first type of cell to take up a portion of the first agent therethrough. Passing a second flow fluid through a flow channel of the microfluidic device, the flow channel being at least partially bounded on a first side by a flexible layer of the microfluidic device and being at least partially bounded on an opposing second side by a rigid layer of the microfluidic device, the second flow fluid including a plurality of a second type of cells therein and a second agent. A control channel is pressurized to a second pressure, a control channel formed in the flexible layer of the microfluidic device such that the flexible layer physically compresses at least one of the second type of cells in the second flow fluid against the rigid layer to induce at least one temporary perturbation in a membrane of the at least one of the second type of cell and permitting the at least one of the second type of cell to take up a portion of the second agent therethrough.

In one embodiment, first flow fluid is passed through the flow channel at a first time point. In another embodiment, the second flow fluid is passed through the flow channel at a second time point.

in one embodiment, the first and second time point are sequential and do not occur at the same time. In one embodiment, the second time point occurs at least 0.1 ms, at least 1 minute, at least 1 hour, at least 1 day, at least 1 week, at least 1 month, at least 1 year, at least 1 decade, or at least 1 century or more after the first time point.

In one aspect described herein, a fluid is passed through a flow channel of a microfluidic device, the flow channel being formed by a flexible layer and a cover layer, the flexible layer including a control channel therein that extends generally perpendicular to the flow channel, the fluid including an agent and a plurality of cells therein; and pressurizing the control channel such that a constriction is formed in the flow channel, and at least one of the plurality of cells in the fluid is physically compressed between the flexible layer and the cover layer at the formed constriction to induce at least one temporary perturbation in a membrane of the one of the plurality of cells and permitting the at least one of the plurality of cells to take up a portion of the agent therethrough.

In one embodiment, the aspect further comprises adjusting a flow rate of the flow fluid in the flow channel.

In one embodiment, the adjusting includes adjusting the flow rate of the flow fluid m the flow channel to zero flow.

In another aspect described herein, a flow fluid is passed through a flow channel of a microfluidic device, the flow channel being formed by a flexible layer and a cover layer, the flexible layer including a control channel therein that extends generally perpendicular to the flow channel, the fluid including an agent and a plurality of cells therein the control channel is pressurized such that it forms a constriction m the flow channel, resulting in the physical compression of at least one of the plurality of cells in the fluid between the flexible layer and the cover layer at the formed constriction; inducing at least one temporary perturbation in a membrane of the at least one of the plurality of cells; and causing the at least one of the plurality of cells to take up a portion of the agent through the at least one temporary perturbation of the membrane.

In one embodiment, pressurizing the control channel causes the compression of the flow channel to occur. In another embodiment, pressurizing the control channel causes the at least one of the plurality of cells to be physically compressed.

In one embodiment, the physical compression of the at least one of the plurality of cells induces at least one temporary perturbation in the membrane of the at least one of the plurality of cells.

In one embodiment, a pressure differential between a pressure inside the at least one of the plurality of cells and a pressure of the flowing fluid causes the at least one of the plurality of cells to take up the portion of the agent through the at least one temporary perturbation of the membrane.

In one embodiment, the at least one of the plurality of cells being physically compressed, a pressure differential between a pressure inside the at least one of the plurality of cells and a pressure of the flowing fluid is insufficient to cause the at least one of the plurality of cells to take up the portion of the agent.

The rate of compression is adjusted by altering the rate of fluid (for example, water) injection through the control channel. Increasing the volume of the control channel results in an increased compression rate in the flow channel.

In one embodiment, the pressure in the control channel is increased at least 1%, at least 2%, at least 3%, at least 4%, at least 5%, at least 6%, at least 7%, at least 8%, at least 9%, at least 10%, 11% at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%. at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more prior to passing the second flow fluid comprising a second type of cell or population thereof and a second agent.

In one embodiment, the pressure in the control channel is decreased at least 1%, at least 2%, at least 3%, at least 4%, at least 5%, at least 6%, at least 7%, at least 8%, at least 9%, at least 10%, 11% at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56% at least 57%, at least 58%. at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%. at least 92%, at least 93%, at least 94%, at least 95%, at least 96%, at least 97%, at least 98%, at least 99% or more prior to passing the second flow fluid comprising a second type of cell or population thereof and a second agent.

One skilled in the art can determine the optimal rate of compression required for individual cell types. Briefly, to determine the rate of compression that induces the highest level of uptake of an agent can be determined by applying various rates of compression to the cell, starting with low compression and gradually increasing the rate of compression. Using a fluorescent agent allows for rapid analysis of agent uptake in the cells e.g, via fluorescence microscopy. The optimal compression rate would be one that induces the highest level of uptake without compromising cell viability as measured by activation of apoptosis or other cell death pathways.

Cellular Uptake

The uptake of molecule is diffusion-based rather than endocytosis i.e., agent(s) to be delivered to a eukaryotic cell are present in the cytoplasm rather than in endosomes following passage through the device. Little or no agent appears in endosomes following cell treatment. For example, large molecules are taken up more slowly than smaller molecules. Controlled compression of the cells leads to superior delivery of target agents while preserving the viability and integrity of the cells. After treatment, cell viability is between 70-100%, e.g., typical viability is 90% after treatment. By comparison, previous delivery methods using high shear rates alone for seconds or milliseconds have been shown to lead to poor viability of cells after treatment. In contrast to prior techniques, the methods of this invention subjects the cells to a pulse of shearing ranging from 100-1000 Pa for a very short perioral of time (approximately 100 microseconds) as the cell passes through the constriction. The present invention, however, are fundamentally different from previous techniques. in the present invention, there is an entire mechanical deformation of the cell as it passes through the compression, which can impose different shearing forces than prior techniques. In some embodiments, the cells are not subject to an electric current. In other embodiments, a combination treatment is used, e.g., mechanical deformation using the device described herein followed by or preceded by electroporation (a type of osmotic transfection in which an electric current is used to produce temporary holes in cell membranes, allowing entry of nucleic acids or macromolecules).

Several parameters can influence the delivery of the agent into the cell. For example, the rate of the compression, the operating flow speeds through the flow channel (e.g., cell transit time to the compression), concentration of the agent in the flow fluid, and the amount of time that the cell recovers/incubates in the flow fluid after compression can affect the absorption of the agent into the cell. Additional parameters influencing the delivery of the agent into the cell can include the velocity of the cell during the compression and a cell compression rate, Such parameters can be designed to control delivery of the agent. The composition of the flow fluid (e.g., salt concentration, serum content, etc.) can also impact delivery of the agent. As the cell is compressed, the deformation/stress induced by the compression temporarily causes perturbations to the cell that causes passive diffusion of the agent through the perturbation. In some embodiments, the cell is only deformed for brief period of time, on the order of 100 μs to minimize the chance of activating apoptotic pathways through cell signaling mechanisms, although other durations are possible (e.g., ranging from nanoseconds to hours). Initial observations described herein have indicated that absorption of the agent by the cell occurs on the order of minutes after the cell is compressed. In some embodiments, the uptake of an agent occurs at least 1 sec after compression. lit other embodiments, the uptake of an agent occurs at least 5 secs, at least 10 secs, at least 20 secs, at least 30 secs, at least 40 secs, at least 50 secs, at least 1 min, at least 2 mins, at least 3 mins, at least 4 mins, at least 5 mins, at least 10 mins, at least 30 mins or more after compression. The time for uptake may vary for different agents.

In some embodiments with certain types of cells, the cells can be incubated m one or more solutions that aid in the absorption of the delivery material to the interior of the cell. For example, the cells can be incubated in a depolymerization solution such as Lantrunculin A (0.1 μl/ml) for 1 hour prior to delivery to depolymerize the actin cytoskeleton. As an additional example, the cells can be incubated in 10 μM Colchicine (Sigma) for 2 hours prior to delivery to depolymerize the microtubule network. These methods can help in obtaining gene expression when delivering DNA.

As described in more detail below with regard to the examples, MACS and the related methods have a broad range of applications. For example, the current subject matter can be applied to regenerative medicine such as to enable cell reprogramming and stem cell differentiation. The current subject matter can be applied to immunology such as for antigen presentation and enhancement/suppression of immune activity through delivery to dendritic cells, monocytes, T cells, B cells and other lymphocytes. Further, imaging and sensing can benefit from improved delivery to target cells of quantum dots, carbon nanotubes and antibodies. Additionally, the current subject matter has application in cancer vaccines and research, such as for circulating tumor cell (CTC) isolation and Lymphoma treatment. The method also provides a robust platform to screen for active siRNA and small molecule compounds capable of treating a disease or manipulating cell behavior.

Figure 8C:
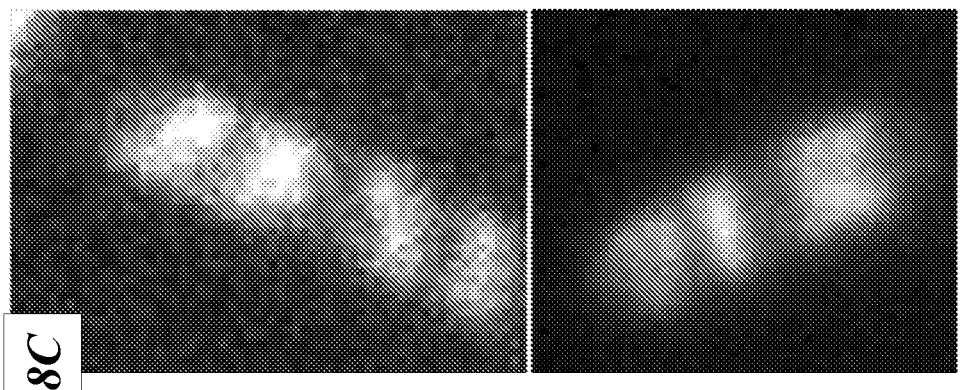
FIGS. 8A-8C show dye uptake upon pressing. The cells are first mixed with propidium iodide and then squeezed by the control layer valve of the MACS device. Top and bottom panels show two different cells (FIG. 8A) brightfield channel (FIG. 8B) propidium iodide fluorescence channel right after pressing (FIG. 8C) propidium iodide fluorescence channel 9 min after pressing.
Figure 8B:
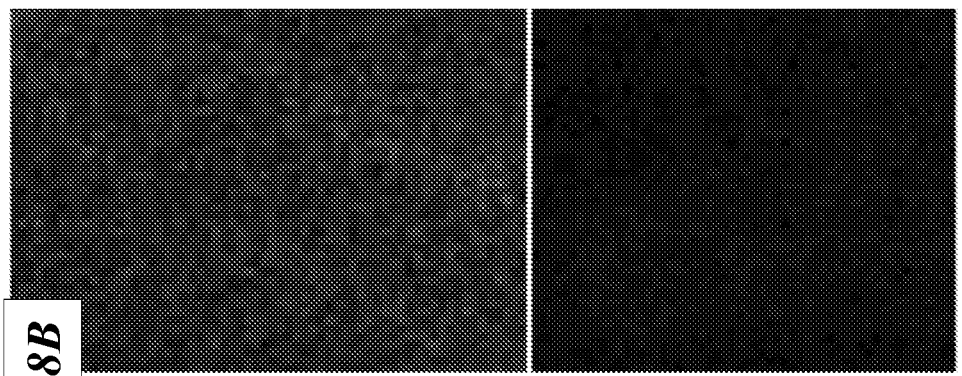
Figure 8A:
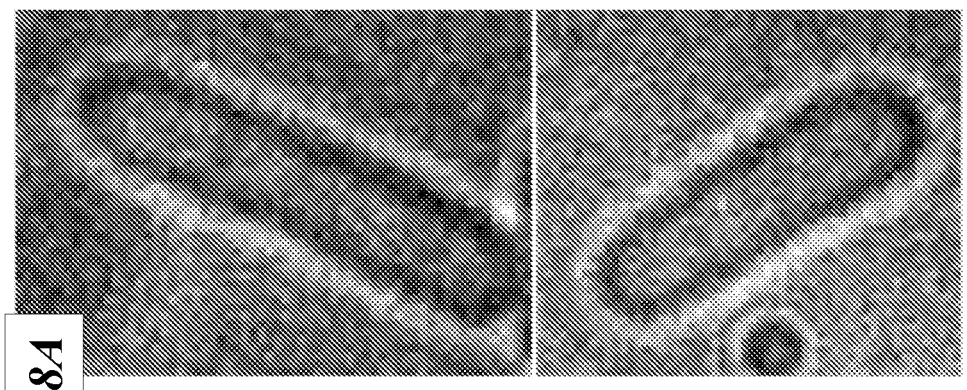

The invention described herein has been successfully demonstrated in one example where the cells were induced to take-up otherwise membrane-impermeable dye (e.g., propidium iodide, FIGS. 8A-8C). Average cell throughput has been measured on the order of 100 cells/minute, and average delivery efficiency has been measured at 50%. All tests were performed at 37° C.

Cell Types

Aspects of the invention describe a system can be used with, for example but not limited to, *E. coli*, fission yeast, mammalian cells, and budding yeast. It is possible to use other cell types, and even artificial cells and liposomes. As a new platform for cell-based, high throughput screening (HTS), the platform can be used, for example, in the pharmaceutical and biotechnology industries for the identification of lead drugs, perform toxicity tests, screen for antibiotics effects, and cam out functional genomics screens. Cells or cell clusters are purified/isolated or enriched for the desired cell type.

In one embodiment, the first type of cell is a eukaryotic cell and the second type of cell is a prokaryotic cell, in another embodiment, the first and second type of cell are different eukaryotic cells, in yet another embodiment, the first and second type of cell are different prokaryotic cells.

Non-limiting examples of type of cells that the first and second type of cell can be include a eukaryotic cell, a prokaryote, a microbial cell, a bacterial cell, a yeast cell, an artificial cell, liposome, a generally rod shape with a diameter that is less than two micrometer and a length that is less than ten micrometers, a generally rod shape with a diameter that is between about 0.2 micrometers and about two micrometer, mammalian cell, oocyte, red blood cell, a white blood cell, a human cell, a cell basing a generally biconcave shape with a diameter that is between about two micrometers and about twenty micrometers, and a cell basing a diameter that is between about one micrometers and about twenty micrometers.

Agents for Uptake

Aspects of the invention described herein relate to the compression of a first type of cell or population thereof to induce the uptake of a first agent, followed by the compression of a second type of cell or population thereof to induce the uptake of a second agent. In some embodiments, the first and second agent are the same. In another embodiment, the first and second agent are different.

Non-limiting examples of an agent that the first and second agent can be include a DNA-staining dye. a fluorescent molecule, a plasmid, a vector, a protein, a nucleic acid, a polypeptide, recombinant DNA. RNA, siRNA, shRNA, miRNA, a compound, a small molecule, an antibody, a virus, a quantum dot (Qdot). a chromosome, a nucleic acid that encode receptors for CAR T-cells, a drug, a therapeutic, an anti-sense oligonucleotide (ASO). an mRNA, an RNA aptamer, a protein aggregate, a protein fibril, a nanoparticle, a poly saccharide, a lipid, an organelle, a mitochondrion, a prokaryote, a microbial cell, and a bacterial cell. An agent can be isolated or purified.

In some embodiments, the agent to be taken up by the cell is present in the flow fluid.

In one embodiment at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more of the cells that pass through the flow channel take up the agent present in the flow fluid following compression.

One skilled in the art can determine whether the agent has been taken up by the cells. For example, the uptake of a fluorescent molecule can be assessed by fluorescence microscopy. In addition, flow cytometry or fluorescence activated cell sorting (FACS) can be used to identify the percentage of cells that have taken up a fluorescent molecule.

Cells are suspended in flow fluid along with the agent to be taken up by the cell. Typical cell concentrations can range, for example from $10^4$ to $10^9$ cells/ml. The concentration of the agent can range from, for example 10 mg/ml to 0.1 μg/ml. The concentration of the agent should be optimized for the individual agent, and can be done by one skilled in the art. The agent may be added to the flow fluid before or immediately after compression depending on the desired setup given that the cellular perturbations remain open for 1-5 minutes. The flow fluid may be composed of a number of salts, sugars, growth factors, animal-derived products or any other component necessary for proper cell proliferation, maintaining cell health or induction of cell signaling pathways. Additional materials may also be added to the flow fluid. For example, surfactants pluronics), antibiotics, and/or bulking materials can be added to the flow fluid.

After the cells are compressed, the cells are allowed to incubate/recover by sitting in the flow fluid. During this time, the cells will uptake the agent present in the flow fluid through the induced perturbations in the cell membrane or wall. One mechanism of uptake is diffusion-based, where larger molecules are absorbed at a slower rate than smaller molecules. The cells are allowed to incubate/recover in flow fluid for on the order of 2-5 minutes, although other durations are possible. In other embodiments, the cells incubate for at least 1 sec, at least 1 min, at least 2 mins, at least 3 mins, at least 4 mins, at least 5 mins, at least 6 mins, at least 7 mins, at least 8 mins, at least 8 mins at least 10 mins, at least 15 mins, at least 20 min, at least 30 mins or more after compression. The time in which cells incubate may vary for different agents and/or cell types. During the time that the cells are incubating/recovering in the flow fluid, material from inside the cell may also release from the cell into the flow fluid. During the incubation/recovery period, certain conditions can be controlled to ensure that delivery quantities of the agent are consistent across the cell population. For example, post-compression, convective delivery mechanisms that impinge agent onto the incubating/recovering cell can be used.

Some embodiments of the technology described herein can be defined according to any of the following numbered paragraphs:

1) A method for uptake of an agent into a cell or population thereof using a microfluidic device, the method comprising:
   a. passing a first flow fluid through a flow channel of the microfluidic device, the flow channel being at least partially bounded on a first side by a flexible layer of the microfluidic device and being at least partially bounded on an opposing second side by a rigid layer of the microfluidic device, the first flow fluid including a plurality of a first type of cell therein and a first agent;
   b. pressurizing a control channel formed in the flexible layer of the microfluidic device such that the flexible layer physically compresses at least one of the first type of cell in the first flow fluid against the rigid layer to induce at least one temporary perturbation in a membrane of the at least one of the first type of cell; and c. causing a portion of the first agent to be taken up by the at least one of the first type of cell through the at least one temporary perturbation in the membrane of the at least one of the first type of cell.

2) The method of paragraph 1, wherein the causing the portion of the first agent to be taken up includes continuing to pass the first flow fluid through the flow channel with the control channel pressurized.

3) The method of paragraph 1, wherein the causing the portion of the first agent to be taken up includes adjusting a flow rate of the first flow fluid through the flow channel with the control channel pressurized.

4) The method of paragraph 1, wherein the causing the portion of the first agent to be taken up includes stopping the flow of the first flow fluid through the flow channel with the control channel pressurized.

5) The method of paragraph 1, wherein the agent is normally cell impermeable.

6) The method of paragraph 1, wherein the agent is a DNA staining dye.

7) The method of paragraph 1, wherein the agent is a fluorescent molecule.

8) The method of paragraph 1, wherein the agent is a plasmid.

9) The method of paragraph 1, wherein the agent is a vector.

10) The method of paragraph 1, wherein the agent is a protein.

11) The method of paragraph 1, wherein the agent is a nucleic acid,

12) The method of paragraph 1, wherein the agent is a polypeptide.

13) The method of paragraph 1, wherein the agent is recombinant DNA.

14) The method of paragraph 1, wherein the agent is RNA.

15) The method of paragraph 1, wherein the agent is siRNA.

16) The method of paragraph 1, wherein the agent is shRNA

17) The method of paragraph 1, wherein the agent is miRNA.

18) The method of paragraph 1, wherein the agent is a compound.

19) The method of paragraph 1, wherein the agent is a small molecule.

20) The method of paragraph 1, wherein the agent is an antibody.

21) The method of paragraph 1, wherein the agent is a virus.

22) The method of paragraph 1, wherein the agent is a quantum dot (Qdot).

23) The method of paragraph 1, wherein the agent is a chromosome.

24) The method of paragraph 1, wherein the agent encodes chimeric antigen receptors (CAR) for CAR-modified T-cells (CAR-T).

25) The method of paragraph 1, wherein the agent is a drug.

26) The method of paragraph 1, wherein the agent is a therapeutic.

27) The method of paragraph 1, wherein the agent is an anti-sense oligonucleotide (ASO).

28) The method of paragraph 1, wherein the agent is an mRNA.

29) The method of paragraph 1, wherein the agent is an RNA aptamer.

30) The method of paragraph 1, wherein the agent is a protein aggregate.

31) The method of paragraph 1, wherein the agent is a protein fibril.

32) The method of paragraph 1, wherein the agent is a nanoparticle.

33) The method of paragraph 1, wherein the agent is a polysaccharide.

34) The method of paragraph 1, wherein the agent is a lipid.

35) The method of paragraph 1, wherein the agent is an organelle.

36) The method of paragraph 1, wherein the agent is a mitochondrion.

37) The method of paragraph 1, wherein the agent is a prokaryote.

38) The method of paragraph 1, wherein the agent is a microbial cell.

39) The method of paragraph 1, wherein the agent is a bacterial cell.

40) The method of paragraph 1, wherein the fluid includes an extracellular growth factor.

41) The method of paragraph 1, wherein the type of cell is a prokaryote.

42) The method of paragraph 1, wherein the type of cell is a microbial cell.

43) The method of paragraph 1, wherein the type of cell is a bacterial cell,

44) The method of paragraph 1, wherein the type of cell is a yeast cell.

45) The method of paragraph 1, wherein the type of cell is an artificial cell.

46) The method of paragraph 1, wherein the type of cell is liposome.

47) The method of paragraph 1, wherein the type of cell has a generally rod shape with a diameter that is less than two micrometer and a length that is less than ten micrometers.

48) The method of paragraph 1, wherein the type of cell has a generally rod shape with a diameter that is between about 0.2 micrometers and about two micrometer.

49) The method of paragraph 1, wherein the type of cell is a eukaryotic cell.

50) The method of paragraph 1, wherein the type of cell is a mammalian cell.

51) The method of paragraph 1, wherein the type of cell is an oocyte.

52) The method of paragraph 1, wherein the type of cell is a red blood cell.

53) The method of paragraph 1, wherein the type of cell is a white blood cell.

54) The method of paragraph 1, wherein the type of cell is a human cell,

55) The method of paragraph 1, wherein the type of cell has a generally biconcave shape with a diameter that is between about two micrometers and about twenty micrometers.

56) The method of paragraph 1, wherein the type of cell has a diameter that is between about one micrometers and about twenty micrometers.

57) The method of paragraph 1, further comprising:

a. passing a second flow fluid through the flow channel of the microfluidic device, the second flow fluid including a plurality of a second type of cell therein that is different from the first type of cell and a second agent;
b. pressurizing the control channel formed in the flexible layer of the microfluidic device such that the flexible layer physically compresses at least one of the second type of cell in the second flow fluid against the rigid layer to induce at least one temporary perturbation in a membrane of the at least one of the second type of cell; and
c. causing a portion of the second agent to be taken up by the at least one of the second type of cell through the at least one temporary perturbation in the membrane of the at least one of the second type of cell.

58) The method of paragraphs 1 to 57, wherein the second agent is the same as the first agent.

59) The method of paragraphs 1 to 57, wherein the second agent is different from the first agent.

60) The method paragraphs 1 to 57, wherein the first type of cell is a prokarotic cell and the second type of cell is a eukaryotic cell.

61) The method of paragraphs 1 to 57, wherein the first type of cell and the second type of cell are a different prokaryotic cell.

62) The method of paragraphs 1 to 57, wherein the first type of cell and the second type of cell are a different eukaryotic cell.

63) The method of paragraphs 1 to 57, wherein the first type of cell and the second type of cell are a different diameter.

64) The method of paragraphs 1 to 57, wherein the first type of cell and the second type of cell are a different shape.

65) A method of using a microfluidic device, the method comprising:
a. passing a first flow fluid through a flow channel of the microfluidic device, the flow channel being at least partially bounded on a first side by a flexible layer of the microfluidic device and being at least partially bounded on an opposing second side by a rigid layer of the microfluidic device, the first flow fluid including a plurality of a first type of cells therein and a first agent;
b. pressurizing, to a first pressure, a control channel formed in the flexible layer of the microfluidic device such that the flexible layer physically compresses at least one of the first type of cells in the first flow fluid against the rigid layer to induce at least one temporary perturbation in a membrane of the at least one of the first type of cell and permitting the at least one of the first type of cell to take up a portion of the first agent therethrough;
c. passing a second flow fluid through the flow channel of the microfluidic device, the second flow fluid including a plurality of a second type of cells therein that is different from the first type of cells and a second agent; and
d. pressurizing, to a second pressure that is different from the first pressure, the control channel formed in the flexible layer of the microfluidic device such that the flexible layer physically compresses at least one of the second type of cells in the second flow fluid against the rigid layer to induce at least one temporary perturbation in a membrane of the at least one of the second type of cells and permitting the at least one of the second type of cells to take up a portion of the second agent therethrough.

66) The method of paragraph 65, wherein the first flow fluid is passed through the flow channel at a first time point.

67) The method of paragraph 65, wherein the second flow fluid is passed through the flow channel at a second time point.

68) The method of paragraph 65, wherein the second time point is a least 0.1 seconds following the first time point.

69) A method comprising:
a. flowing a fluid through a flow channel of a microfluidic device, the flow channel being formed by a flexible layer and a cover layer, the flexible layer including a control channel therein that extends generally perpendicular to the flow channel, the fluid including an agent and a plurality of cells therein; and
b. pressurizing the control channel such that
i. a constriction is formed in the flow channel, and
ii. at least one of the plurality of cells in the fluid is physically compressed between the flexible layer and the cover layer at the formed constriction to induce at least one temporary perturbation in a membrane of the one of the plurality of cells and permitting the at least one of the plurality of cells to take up a portion of the agent therethrough.

70) The method of paragraph 69, further comprising adjusting a flow rate of the flow fluid in the flow channel.

71) The method of paragraph 69, wherein the adjusting includes adjusting the flow rate of the flow fluid in the flow channel to zero flow.

72) A method comprising:
a. passing a flow fluid through a flow channel of a microfluidic device, the flow channel being formed by a flexible layer and a cover layer, the flexible layer including a control channel therein that extends generally perpendicular to the flow channel, the fluid including an agent and a plurality of cells therein;
b. pressurizing the control channel;
c. forming a constriction in the flow channel;
d. physically compressing at least one of the plurality of cells in the fluid between the flexible layer and the cover layer at the formed constriction;
e. inducing at least one temporary perturbation in a membrane of the at least one of the plurality of cells; and
f. causing the at least one of the plurality of cells to take up a portion of the agent through the at least one temporary perturbation of the membrane, 73) The method of paragraph 72, wherein pressurizing the control channel causes the compression of the flow channel to occur.

74) The method of paragraph 72, wherein pressurizing the control channel causes the at least one of the plurality of cells to be physically compressed.

75) The method of paragraph 72, wherein the physical compression of the at least one of the plurality of cells induces at least one temporal) perturbation in the membrane of the at least one of the plurality of cells.

76) The method of paragraph 72, wherein a pressure differential between a pressure inside the at least one of the plurality of cells and a pressure of the flowing fluid causes the at least one of the plurality of cells to take up the portion of the agent through the at least one temporary perturbation of the membrane.

77) The method of paragraph 72, wherein prior to the at least one of the plurality of cells being physically compressed, a pressure differential between a pressure inside the at least one of the plurality of cells and a pressure of the flowing fluid is insufficient to cause the at least one of the plurality of cells to take up the portion of the agent.

EXAMPLES

Example 1

MACS for Microfluidics-Assisted Cell Screening (MACS) works by injecting cells through a flow channel and gently compressing the ceiling of the channel. This setup improves the statistical power and automation capabilities of microscopy while retaining or even increasing the sensitivity of imaging of non-adherent cells. It works for a wide range of cell types, sizes, and shapes without modifying the device dimensions, while keeping cells in the chosen growth medium with minimal perturbations until the moment of imaging. MACS is compatible with the 96-well plate format and makes it possible to capture exceedingly rare cells in a population. For $E.\ coli$, it was further shown that MACS allows us to exert controlled pressure to slightly flatten and widen the cells, presumably by expelling some water molecules. The diffusion of cytoplasmic proteins then slows down by orders of magnitude enough to ensure that fluorescent proteins do not move away from a diffraction-limited spot during typical exposure times in fluorescence imaging 7, 11. The fluorescent proteins thus effectively behave as if they were temporarily fixed. As opposed to chemical fixation, this procedure does not quench the fluorescence signal, and makes it possible to accurately identify single fluorescent proteins in cells. It was previously quantified this effect by applying the method to single fluorescent proteins as well as fluorescent proteins-fluorescent protein fusions, by counting photo-bleaching steps[11], and by comparing the results to other methods[10], showing that the approach makes it possible to accurately count the number of fluorescent proteins per cell even when cells contain just one or two protein copies[10]. The flattening of cells in the z-dimension and widening in the x-y plane also helps with counting in three ways: by reducing the projected auto fluorescence per area unit and thereby increasing the signal-to-noise ratio for FP detection, by further separating the proteins from each other to reduce the risk of spatial overlap, and by making it possible to keep the whole cell in focus. Increasing the pressure further compresses cells enough to make them take up compounds that otherwise could not cross the membrane, or to evaluate cell membrane or cell wall mutants.

MACS capitalizes on the polydimethysiloxane (PDMS)-based, microfluidic, on-chip valve developed by Quake and co-workers[12] and consists of two layers: cells are injected through a flow channel, while a control layer that runs above perpendicular to the flow channel can be pressurized to collapse the flow channel ceiling on cells. The simple design, straightforward operating principle, and the utilization of well-characterized valves render MACS robust and reproducible. The valves themselves can be actuated millions of times without signs of fatigue, and the major limitation for long-term stability of MACS is instead the eventual accumulation of debris at the intersection of the control channel and the flow channel. Optimizations were carried for cell loading into the chip, surface passivation, and media preparation to minimize debris, designed cleaning protocols, and fabricated chips with an array of individual control/flow channel intersections to be able to switch to new intersections after debris builds up.

The MACS platform is cheap to build and compatible with a wide range of cell types and microscopes. However, the original setup was involved and required extensive tailoring. A more streamlined and standardized platform is presented herein, including detailed steps for building and using the setup as well as the code for data acquisition and analysis. Although the experiments described here are carried out on $E.\ coli$ cells, the setup works for a wide range of non-adherent cell types[11].

Microfluidics Device Design and Fabrication.

Described herein is a protocol for fabricating and assembling the flow and control layers of the PDMS MACS chips using soft-lithography. In brief, a UV light is used (FIG. 5A) and patterned transparency masks (FIG. 5B) to etch desired features into a layer of photo resist (PR) deposited onto clean silicon wafers to create negative master molds for each layer. The actual PDMS is ease on each and align them.

More specifically, the AutoCAD is first used to design high-resolution transparency masks (Output city) for the pattern in the flow and control layers. Maximum resolution for printing this mask is recommended, using the emulsion-side down (i.e. features are printed on the non-glossy side), to ensure minimal distances between the printed side of the mask and the PR on the wafer. A detailed, step-by-step protocol is described in the PROCEDURE section.

Figure 5A:
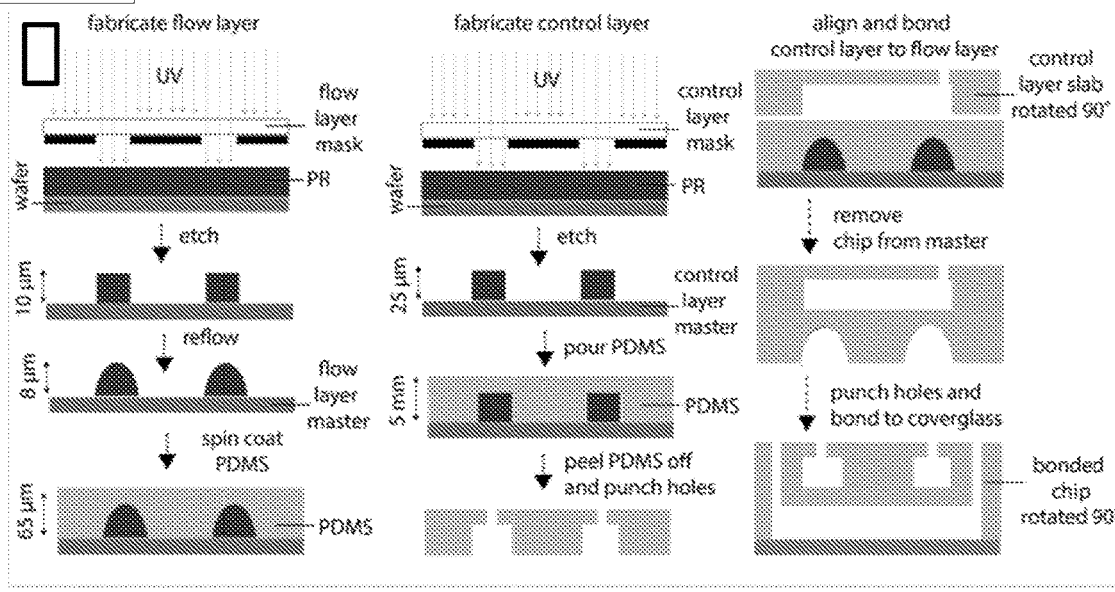
FIGS. 5A-5C shows the MACS fabrication.
Figure 5B:
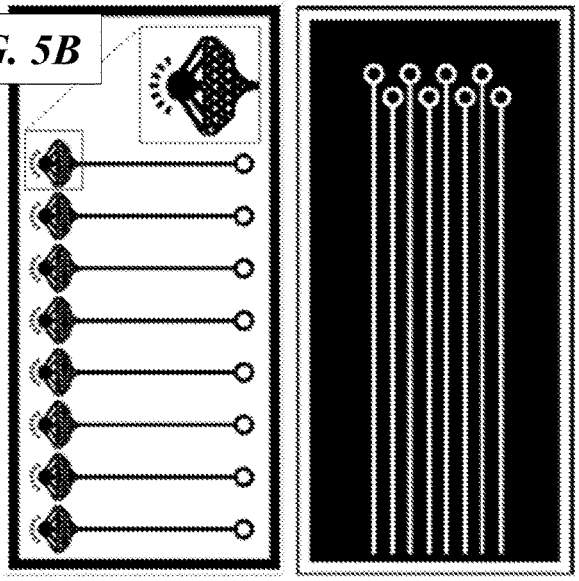

The silicon wafers are cleaned by sequentially squirting generous amounts of acetone, methanol and Milli-Q water (Millipore Corporation) while spinning the wafers on a spin-coater. The wafers are dried for 5 min on a 65° C. hotplate before using the spin-coater to deposit positive PR AZ10xt (AZ Electronic Materials) to a height of 10 μm on top of the wafer. The transparency mask is illuminated with UV light to etch out the desired pattern in the PR (FIG. 5A), and the wafer is subsequently heated to round of the rectangular channels into dome-shapes (aka reflow) with a final channel height of ~8.5 μm, which is essential for proper valve closure[12]. The wafer is baked on a hotplate overnight to stabilize the positive PR A master mold for the simpler control layer of the device is similarly built, by spin-coating the negative PR SU-8 2025 (MicroChem) to a 25 μm thickness on a wafer, and UV patterning it using the transparency mask for the control channels. These steps produce the silicon masters from which the PDMS chips are molded (FIG. 5A).

Figure 5C:
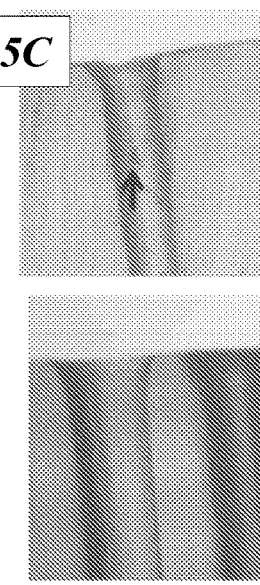
Figure 6:
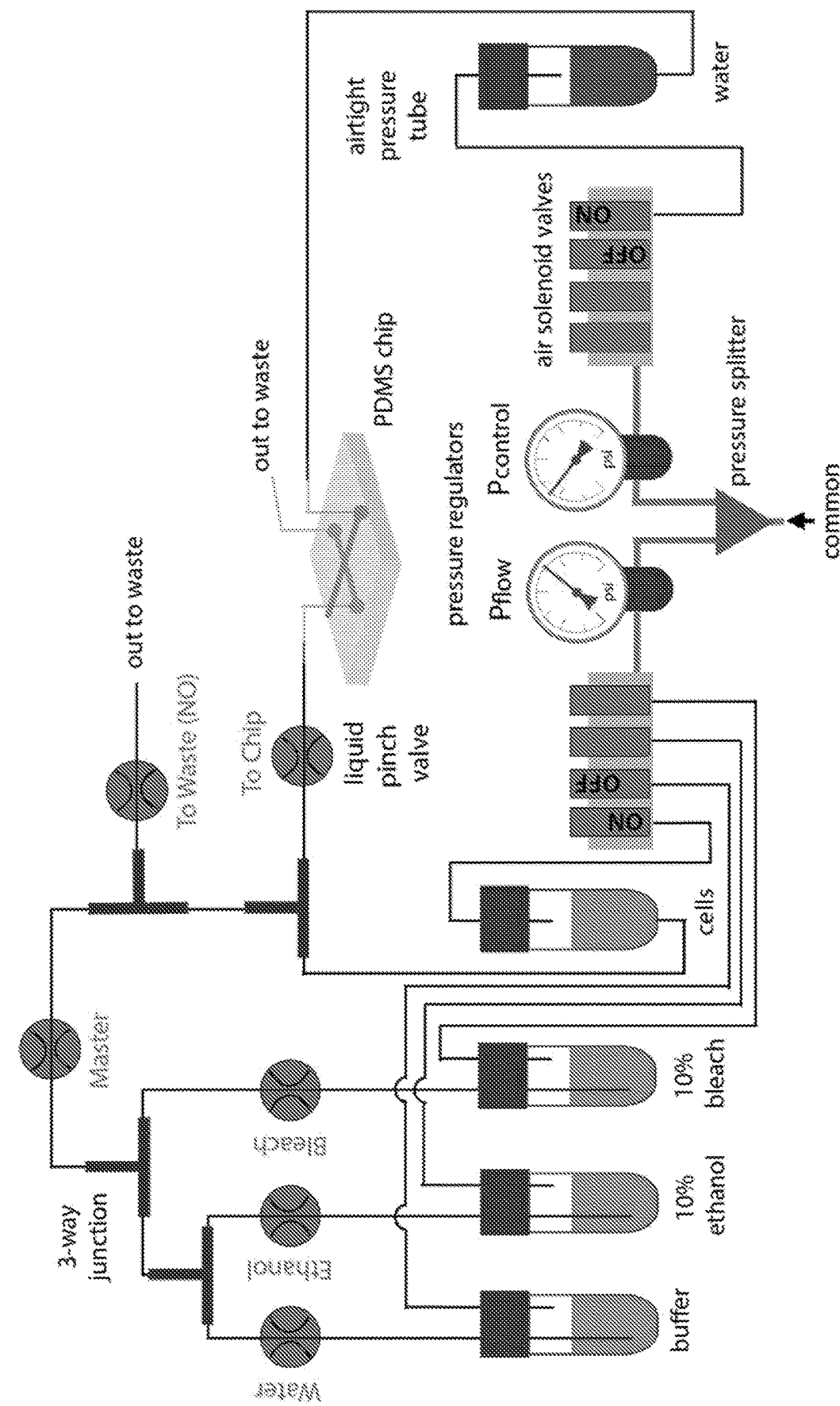
FIG. 6 shows a detailed schematic of automated imaging with MACS. Pinch valves ensure unidirectional flow and flow selection. After each sampling, a cleaning routine is done by rinsing the pressure tube for cells (PT) and the MACS chip. A normally open (NO) pinch valve allows rapid discarding of the leftover rinsing liquids into the waste.

PDMS is mixed from a two-part silicone elastomer kit (Slygard 184, Dow Corning), consisting of a base (part A) and curing agent (pan B) in particular weight ratios (pan A:part B) To produce the MACS chips from the masters, a spin-coat 20:1 PDMS on the flow channel master at 1250 rpm for 45 sec to yield a ~65 μm thick PDMS membrane. With this thickness and PDMS ratio, the minimum pressure required to close the valve is ~5 psi. If even gentler cell handling is required, a thinner membrane can be made to allow the valve to close at lower pressures. For the control channels, 5:1 PDMS is poured onto the control layer master. After both layers are partially cured at 65° C. for 33 min, PDMS is peeled off the control layer master, punch holes through the inlets and align the control channel slabs to the flow channel. Both layers are cured for another 4 h at 65° C. to achieve thermal bonding, and cut out the now two-layer chips from the flow-layer wafer using a new razor blade. Holes are punched in the two-layer chips and sonicate them in isopropanol for 30 min to remove debris (FIG. 5C)

produced during hole punching. The chips are rinsed with Milli-Q water and sonicate in Milli-Q water for 30 min before leaving the chips to dry for 4 hours at 65° C. Finally, the two-layer PDMS chips permanently plasma bonded to glass coverslips. Freshly bonded chips are kept at room temperature for at least one day to regain the native surface properties following plasma treatment.

Basic variations to the protocol can be made depending on the requirements of a given application. For instance, for specific applications, such as maximizing throughput, it may be necessary to alter the device dimensions, in which case, other parameters (such as pressure or PDMS membrane thickness or stiffness) also need to change to maintain optimal performance. For the stiller MACS chips used for mechanical slowing down of diffusion of cytoplasmic molecules, the chips are left at 65° C. for 3 days after plasma bonding to cover glass. Alternatively, the stiffness of the PDMS membrane can be increased by using an A:B ratio greater than 20:1. In some applications, e.g. when assessing mechanical integrity of cell wall mutants or squeezing cells to force them to uptake material, even higher pressure is required. For such devices, both the flow and the control channels are produced with 10:1 or even 5:1 PDMS, and bond them together using oxygen plasma, resulting in an even stiffer chip.

Operating Principle of MACS and Automation.

To inject cells or collapse the control layer, liquids pushed out from airtight pressure tubes (PT). Introducing pressurized air into the pressure tube drives out liquid, either into the flow channel or used to pressurize the control layer to push the valve downwards. MACS is thus based on imaging cells that pass through flow channels while regulating pressures to partially or completely collapse the flow channel ceiling. Driving flow with air pressure rather than syringe pumps allows for easy streamlining and fast response times.

Figure 1B:
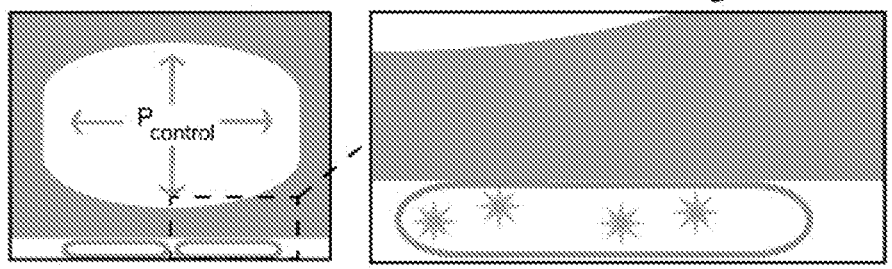

When operating MACS, the simplest scheme of simply collapsing the valve after slopping the flow yields extremely poor trapping efficiency due to the rapid displacement of liquid. Instead, MACS relies on three distinct valve states— open, half-open, and closed—which are achieved by controlling both the pressure of the control valve (Pcontrol) and the pressure driving the flow (Pflow) of the cells (FIG. 1A). Depending on the pressures applied to control and flow channels, this causes cells to flow rapidly through the flow channel (FIG. 1A, left), trickle through the flow channel in a monolayer (FIG. 1A, middle), be gently held against the cover slip (FIG. 1A, right), or be squeezed against the cover slip with greater pressure (FIG. 1B).

After setting up the chip, mounting it on the microscope, and identifying a valve intersection, cells are injected into the chip. After cells arrive at the imaging FOV, the Pcontrol is turned on. The recommended setting Pcontrol=20 psi for a chip with the dimensions reported here. The next step is to identify the appropriate flow rate to achieve the half-open state. Specifically, the half-open state operates with (Pflow, Pcontrol)=(on, on) but in order to achieve the actual half-open state where cells trickle between PDMS and coverglass, it is necessary to adjust the magnitude of Pflow to a level that is just high enough to break the seal between PDMS and the coverslip. This occurs at a value of Pflow~18 psi for a chip with typical dimensions, given Pcontrol=20 psi. When the pressures are chosen properly and (Pflow, Pcontrol)=(on, on), the cells should start slipping through the FOV as a monolayer. When the flow is stopped (Pflow, Pcontrol)=(off, on) the closed state is achieved. Just before image acquisition, the value of Pcontrol can be re-adjusted depending on the imaging requirements. For instance, in single-molecule counting experiments, Pcontrol is set to 30 psi just prior to imaging. An imaging cycle thus consists of introducing new cells in the open state, trapping cells by transitioning from the open to the half-open to the closed state, and then imaging cells compressed with the desired pressure. Each cycle typically takes ~2-15 s (corresponding to ~240-1800 frames per hour), but even higher throughput can be achieved by using large channels and an automated stage (see below). Cells are generally trapped in a subregion of the total footprint of the valve intersection (approximately 100 μm×50 μm out of 200 μm×200 μm), which can be varied with slight modifications of Pcontrol and Pflow.

Compressing cells in this controlled manner can slow down the diffusion of cytoplasmic fluorescent proteins (FPs) almost 100-fold, allowing us to detect them on a standard total internal reflection fluorescence (TIRF) setup with minimal perturbations until the moment of imaging, as is extensively characterized elsewhere[11]. Although this can in principle be achieved by simply using higher pressure (as in FIG. 5B), a better performance is achieved by using stiffer PDMS chips rather than higher values of Pcontrol, since using higher pressure increases the risk of delaminating the microfluidic chip.

Application 1: High-Throughput Imaging.

As a proof-of-concept for the stability and throughput capabilities of MACS, unattended snapshots of approximately $10^6$ E. coli cells were acquired in a 4-hour time window at a single valve intersection. Conventional automated xy-stages can achieve a comparable performance in terms of sampling speed, but cells are then kept on the surface for long time periods before imaging, which can change their properties. MACS, on the other hand, keeps cells growing in the desired medium and brings in a fresh sample every time.

To achieve a throughput of 500-5,000 cells/min depends on parameters such as magnification, trapping area, cell density etc. Typically, 250× magnification (100× objective combined with 2.5× camera lens) is used for the single-molecule counting, and 60-100× for high-throughput data acquisition. For larger cells, lower magnification can be used to retain high throughput. Rather than carrying out distinct cycles of cell trapping and imaging, MACS can also run constantly in the half-open valve state to flow a stream of cells through the FOV (FIG. 7A). This sacrifices image quality somewhat but can be used to detect rare phenotypes, for example where the readout is fluorescence levels above some threshold, or the presence of a localized signal.

The throughput of MACS is limited by the time between successive rounds of cell trapping and on a longer time scale, by the eventual accumulation of debris in the FOV. Debris accumulation is only problematic during actuation of the valve and the presence of sample flow. Debris does not get stuck permanently and is eventually washed away unless pressed against. If the intersection used does get filled with debris, one of the many unused intersections on the same chip can be used for imaging, since intersections not actively in use, do not collect debris. The time between rounds of cell trapping is typically dominated by the time it takes cells to stop moving when the channel is in the closed state ($t_{closed}$). Optimizing $t_{closed}$ for each application is recommended since the sensitivity to such movement depends on the experiment. For single-molecule counting experiment, it is often a 15 sec ($t_{closed}$=15 sec) wait, but often the wait is only 1-5 sec when exact localization of single molecules is not required. The optimal value for $t_{closed}$ may also display chip-to-chip variability and depends on factors such as cell density and cell type.

If the FOV of the camera is small compared to the total cell trapping area, a substantial speed-up can be achieved by using an automated stage and moving the FOV to cover the entire trapping area. When even greater throughput is needed, it is also possible to modify the dimensions of the chip to fabricate larger valves and thus larger cell trapping areas. In principle, it could also be possible to run and image several intersections simultaneously to increase throughput further.

For a given cell density in the medium, the coverage within the FOV can be adjusted by simply changing parameters such as Pflow and Pcontrol as well as the duration of the half-open state. Modifying cell density is particularly important for the single-molecule counting assay, because it is hard to exert enough pressure on each individual cell to slow down diffusion in areas with very high local density of cells.

Reducing the cell density can also be important, e.g. when carefully quantifying fluorescent levels between cells, since the point-spread function of light can cause light emitted from one cell to be attributed to its neighbor cells. Cells in areas of high cell density can then artificially appear brighter. On the other extreme of low cellular density (e.g. the balanced growth in bacteria), MACS can function as a concentration device since the half-open state can function locally as a 'sieve' and permits gathering statistics that would not be possible via traditional sample preparations (such as agar pads), which simply spread cells on cover glass surfaces.

Application 2: Retrieving Cells With Rate Phenotypes.

The setup can also be used to screen large numbers of cells, identify rare cells of interest for higher-quality imaging, and then retrieve those cells into test tubes. For example, it is possible to run MACS in the highest throughput mode, where cells are constantly moving through the device and imaged in video mode as they trickle by (FIG. 7A), and use real-time image analysis to identify cells of interest. By instantaneously switching to the closed state, those cells can be trapped for high-quality imaging. To illustrate this capability, a cell culture of an *E. coli* strain expressing GFP is taken and spiked it with a few cells from an RFP expressing strain. On-the-fly image processing allowed for detection of the cell of interest (i.e., a red cell) as it appeared within the FOV (FIG. 7B). Although the detection rates depend on multiple parameters such as flow rate, cell density, and the closing properties of the valve, in our trial runs, cells diluted 1:10,000 and 1:100,000 were detected within, on average, 3 seconds and 30 seconds, respectively. This allows us to estimate the occurrence probability of rare phenotypes of interest, and then characterize those phenotypes with more detailed imaging.

Figure 7D:
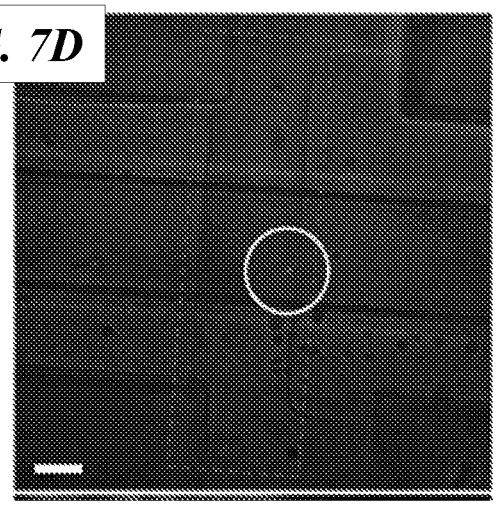
Figure 7E:
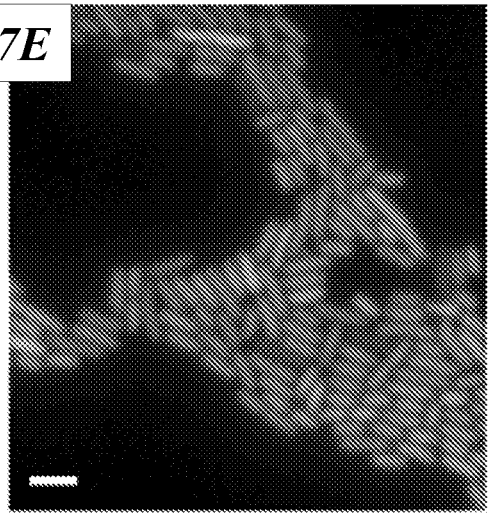

Minor modifications to the design make it possible to retrieve the trapped cells from the device, allowing us to enrich or even directly isolate rare phenotypes (FIG. 7C). In this modified design, two inlets and outlets are controlled via on-chip valves (valves 1-4). During screening, the MACS device is in the half-open state and cells are imaged as they flow past the FOV to the waste (valves 3 and 4 are closed, and valves 1 and 2 are open). When a rare FOV with the cell-of-interest is detected (FIG. 7B), cell flow is stopped immediately, thus switching the MACS device to the closed state. At this point, detailed images can be acquired, if needed. Next, all inlet and outlet valves (valves 1-4) are closed, and release the control valve (FIG. 7D). Then valves 3 and 4 are opened allowing oil to flow into the chip and sending the trapped volume out for collection. When cells grew overnight and imaged on agar pads, it was observed that the RFP-expressing cells were highly enriched (FIG. 7E). Using an oil phase for cell collection provides precise control of the volume that is retrieved. To facilitate the collection using the oil phase, the chips are treated with a commercial water repellent[14] (Aquapel) after plasma bonding. These chips are kept at room temperature until use.

Application 3: High-Pressure MACS for Single-Molecule Imaging and Intracellular Delivery.

Described herein is the method for how this setup can be used to image cells of varying sizes and shapes with high throughput, without tailoring the exact dimensions of the device, while keeping cells in the desired growth medium until the time of imaging to reduce stress, and even retrieving rare cells of interest. However, perhaps the most striking feature of this device is that it allows us to apply pressure in a controlled way to cells, such that the diffusion of cytoplasmic proteins can be slowed down by two orders of magnitude[11]. Without wishing to be bound by theory, it is believed this reflects the interesting finding that the *E. coli* cytoplasm is close to a glass transition[15], where slightly compressing cells expels some of the water from the cytoplasm and appears to make the movement of cytoplasmic proteins transition from almost free diffusion to crowding.

Regardless of the underlying mechanism it was found that the slowing down of diffusion allows for visualization and even accurate counting of fluorescent proteins at exceptionally low abundances, using conventional TIRF microscopy setups [10,11]. As opposed to chemical fixation protocols, this mechanical fixation can be achieved with no loss of fluorescence, and extensive controls with photobleaching steps and tandem dimer FPs[11] indicated close to all mature fluorescent molecules were detected.

The increased pressure also flattens cells, which improves counting in several ways. First it ensures that the autofluorescense is lower per projected area of the imaged cell, thereby reducing the background for counting. Second it can ensure that more of the cell is within the imaging focal plane. In fact, for *E. coli* growing in rich media, imaging setups typically keep most of the cell in focus, but not entirely. Mild flattening is then enough to achieve focus throughout the cytoplasm. Third, by 'pancaking' cells slightly the projected area is greater, which reduces the probability that individual molecules will have overlapping point-spread functions and therefore cannot be separated.

Practically, the increase in effective pressure was found to be the easiest to achieve by using stiffer PDMS chips. Specifically, it is recommended to keep the chips at 65° C. for three days after plasma bonding to coverslips to achieve enough stiffening to induce cytoplasmic, slowing down. Unless the pressure is greatly increased, which can cause other problems, pressing the chips without such 'aged' chips does not cause sufficient slowing down to visualize proteins within the typical 10-100 ms integration times of the CCD camera. For single-molecule imaging it also becomes critical to properly clean the glass surfaces, or else fluorescent background spots can masquerade as actual fluorescent proteins. A cleaning protocol described by Elf et al. is recommended to clean glass coverslips[16]. Alternatively, glass coverslips can be kept under oxygen plasma for 10 min. It is also essential to wear gloves throughout since touching the involved surfaces with bare hands can cause substantial fluorescent impurities. The growth media can also introduce fluorescent particulates. For *E. coli*, it was found that the standard LB broth, which is highly fluorescent, can be substituted for M9 media supplemented with 10% LB without compromising the growth rate but greatly reducing false positive counts due to fluorescent impurities.

The MOPS-based rich defined medium EZRDM (Teknova) works even better for this purpose. By paying close attention to dealing procedures at different stages, as few as 0.3 spots/cell can be achieved for a control strain that docs not express the fluorescent proteins[10].

Another feature of MACS is the observation that compressing cells in the closed slate forces them to uptake molecules. Specifically, extra stiff chips are used, made by plasma bonding two 10:1 PDMS layers, cells can be pushed on harder causing them to uptake a DNA-staining dye that is normally cell impermeable (propidium iodide. Thermo Fisher) (FIGS. 8A-8C). This procedure also allowed us to distinguish wild type cells and cell wall mutants, since the latter uptake more dye at lower pressures than the wildtype.

Integration of Growth Chamber.

Figure 9:
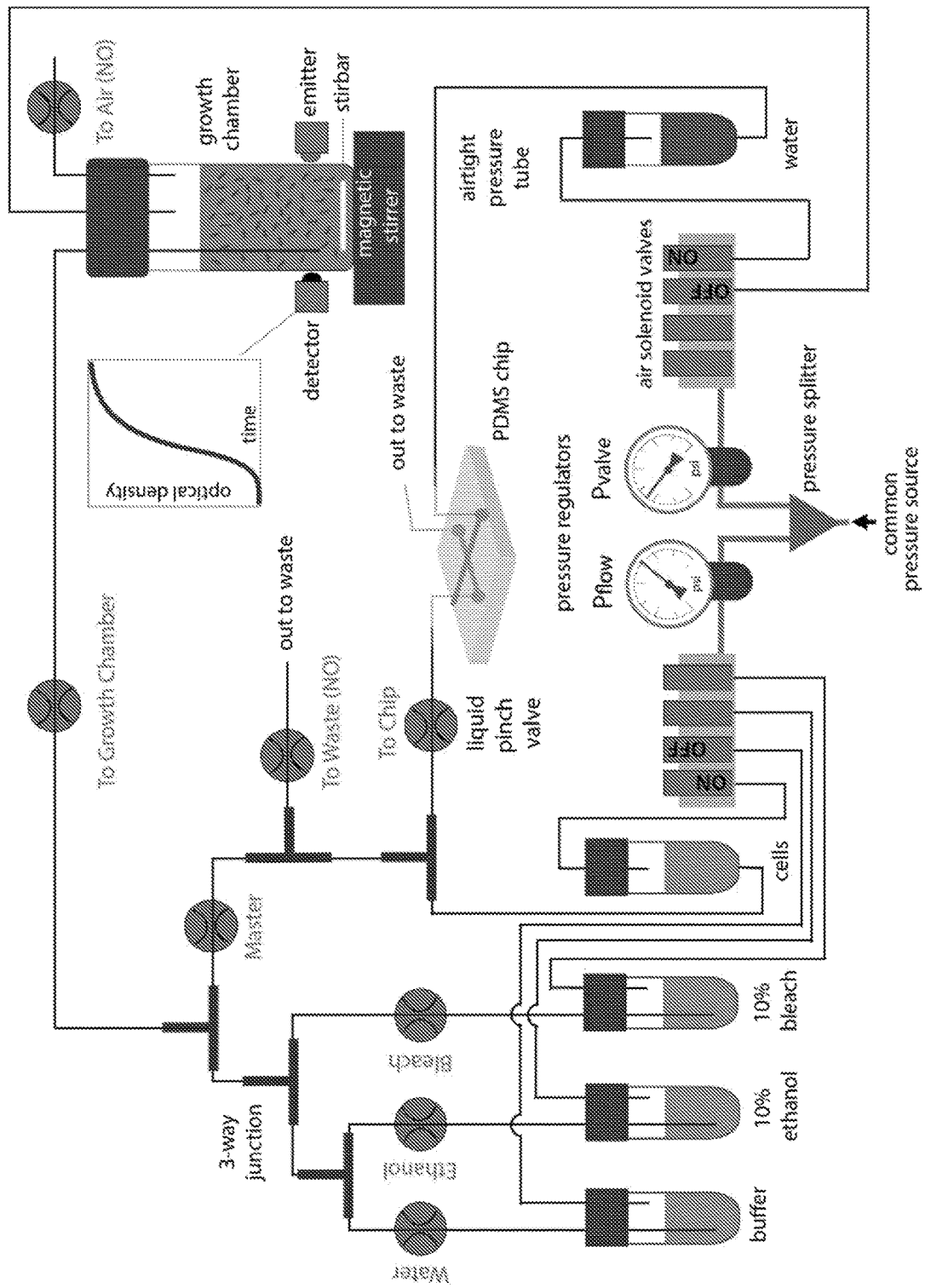
FIG. 9 shows integration of growth chambers with MACS. Schematic showing sampling from a growth chamber where the optical density of a growing culture can be monitored in real time. Passive aeration of the culture is achieved through the normally open (NO) pinch valve, which is connected to open air by delimit. The pressure to the growth chamber is turned, close the 'To Air' pinch valve, open the 'To Growth Chamber' pinch valve and open the 'Master' pinch valve causing cells to flow from the growth chamber to the PT. The detector—placed at 180° with respect to the emitter measures the transmission of light through the sample, which serves as a metric for optical density (OD600) after calibration (Toprak, E., et al. *Nat Protoc* 8(3):555-67, (2013)).

It is possible to incorporate a growth chamber upstream of MACS, allowing for on-demand microscopy coupled to real time monitoring of population density, e.g. using batch cultures or turbidostats. This is particularly convenient when studying population dynamics of multiple cell types that change in density over time. A complete schematic of a growth chamber incorporated with MACS is shown in FIG. 9. It is suggested that paying attention to the aeration needs during the growing culture. This configuration docs not necessarily allow for optimal aeration without other modifications, since the rigorous stirring or shaking required for optimal aeration can interfere with $OD_{600}$ measurements. For experiments that require active aeration or shaking, the $OD_{600}$ measurements can be separated from the growth flask. A detailed description of this setup is in preparation. With further modifications, it is possible to implement treatment of the samples with drugs or inducers without affecting the rest of the growing cell culture. The growth chamber can be modified to run in specialized modes, such as turbidostat or chemostat, by using peristaltic or solenoid pumps.

This single, simple device serves many purposes—increasing throughout compared to conventional microscopy, ensuring that cells can be grown in the desired liquid culture until moments before imaging in 96 well plates, if desired, retrieving rare cells of interest, pressing on cells to achieve accurate mechanical fixation to count individual includes and squeezing cells to force them to uptake chemicals that otherwise could not pass through the membrane. Though MACS docs not have the advantage of tracking cell lineages that some other microfluidic devices provide, it also does not need to be precisely tailored to the exact cell sizes and shapes of a given sample, as is required to use those devices. In fact, the same device can simultaneously be used for cells that vary >100-fold in volume. It can also serve as an orthogonal test that growth chamber methods truly reflect cell growth in suspension cultures.

Figure 10:
FIG. 10 shows single-molecule counting in *E. coli*. Left. (Top) The analysis code outlines the cell boundary and displays the spots detected from single molecules of SprE-mNeonGreen within individual cells. (Bottom) Population-wide distribution of SprE abundance. The experimental data (blue bars) is shown overlaid with a theoretical Poisson distribution (red dots) of the same average.
Figure 10:
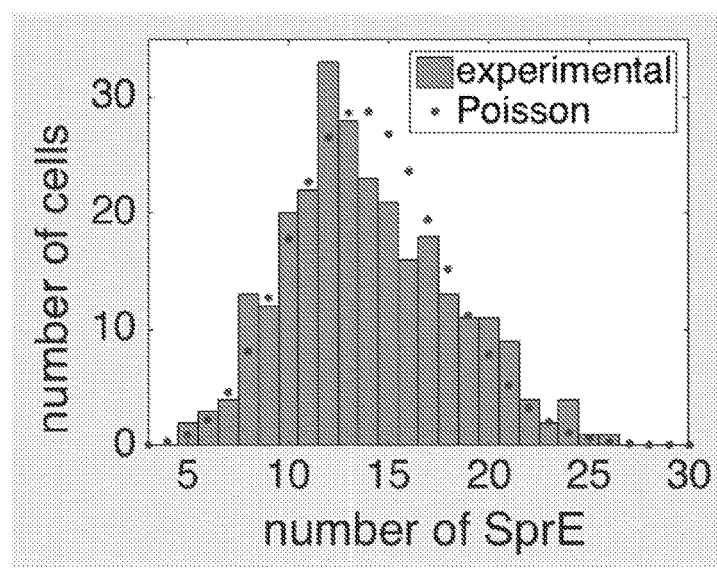

For the single-molecule counting measurement, an *E. coli* strain where a low-abundance protein (SprE) had been fused to GFP (mNeonGreen) is used at its native chromosomal locus. An exogenous copy of a second fluorescent protein (CFP) on the chromosome served as a segmentation marker and allowed identification of cells and their boundaries (FIG. 10). For this experiment, chips that had been cured for 3 days at 65° C. after fabrication and thus were stiffer were used. Cells were injected, accumulated in the half open state, and trapped with an imaging pressure (Pcontrol) of 30 psi. Approximately 15 seconds after trapping, cells were imaged using a 50 mW 514-nm laser with HILO modality on an EMCCD camera at video rate (33 Hz. i.e. 30 msec exposure time). The provided MATLAB code, AnalyzeMacsInteractively, was used to analyze the data, see Supplementary Manual for a detailed description of using the code. Under these growth conditions, the average number of SprE per cell w as ~14 and the population-wide distribution of SprE abundance is close to Poissonian.

Running MACS in the continuous mode, *E. coli* cells were detected that are proficient in plasmid conjugation a leading cause of horizontal gene transfer and the spread of antibiotic resistance genes. Because the expression of transfer (tra) genes is associated with higher metabolic burden and increased sensitivity to male-specific phages, many conjugate plasmids are naturally repressed[18]. For example, under laboratory conditions, it is known dial plasmid R1 turns on the conjugation machinery at frequencies below $10^{-3}$ per cell and generation[19], but even order-of magnitude estimates have proven challenging because the events are so rate. To identify these rate events a c/p gene was placed at the very end of the transfer operon and used MACS to identify cells expressing CFP (data not shown). Data suggests that the tra operon is activated at a frequency of approximately $10^{-6}$ per cell and generation, under our conditions.

Example 2

Delivery of DNA or RNA Molecules Into Leukocytes.

Peripheral blood mononuclear cells (PBMCs) are isolated from human whole blood using a density gradient centrifugation method with Ficoll-Hypaque as described (sec e.g. I. J. Fuss, et al., Isolation of whole mononuclear cells from peripheral blood and cord blood, *Curr Protoc Immunol.*, Chapter 7 Unit 7.1., (2009)). Leukocytes are isolated from PBMCs following a published protocol (see e.g. S. Arimilli. et al., Rapid isolation of leukocyte subsets from fresh and cryopreserved peripheral blood mononuclear cells in clinical research, *Cryo Letters*, 33(5) 376-84. (2012)). T cell subpopulations of special interest are further enriched using antibodies against specific CD (cluster of differentiation) surface markers (including but not limited to CD3, CD4 or CD8) for positive/negative selection and fluorescence activated cell sorting (FACS) or magnetic activated cell sorting (MagniSort Cell Separation Technology, ThermoFisher Scientific). Purified human T cells can also be purchased from a vendor (e.g., Astarte Biologics). For intracellular delivery, the leukocytes or purified cells are first suspended in the desired growth medium or in 1× PBS with supplements (e.g., 3% FBS) and then mixed with the nucleic acids (e.g., plasmid DNA or mRNA) that encode the protein of interest (e.g., a chimeric antigen receptor or a GFP marker). The flow fluid is optionally pre-incubated for up to 1 hour at 37° C.; or directly run through the flow channel of the MACS device to enable intracellular uptake of the nucleic acid molecules. For T cells that are modified to express a chimeric antigen receptor (CAR), functional testing and proof-of-concept studies are performed as previously described (see e.g. E. J. Cheadle, et al., Chimeric antigen receptors for T-cell based therapy, *Methods Mol Biol*, 907:645-66 (2012)).

Example 3

Delivery of Recombinant Proteins Into Red Blood Cells (RBCs).

The MACS device is used to deliver a recombinant protein (e.g., phenylalanine hydroxylase or a GFP marker) into the cytoplasm of red blood cells (RBCs). Blood is collected from a patient by venipuncture performed by one skilled in the art, for examples a trained phlebotomist. RBCs are isolated from the patient's blood following a standard protocol. In short, the blood (e.g., 10 ml) is centrifuged for 5 min at 500 g to separate hematrocrit (red., lower layer) from plasma (yellowish, upper layer), which is then gently aspirated with a micropipettor and discarded. The hematocrit fraction is resuspended with 150 mM NaCl to a total volume equivalent to the original volume of the blood sample, and the final solution is centrifuged for 5 min at 500 g. This wash step is repeated twice, and the supernatant is replaced with 1× PBS (pH 7.4) after the final centrifugation step. The purified RBCs are mixed with the recombinant enzyme (e.g., 0.1 to 10 mg mi) and the solution is run through the MACS device to enable intracellular uptake of the recombinant enzymes. The loaded RBCs are collected from the outlet of the MACS device and temporarily stored (see e.g. J. R. Hess, An update on solutions for red cell storage, *Vox Sang*, 91(1):13-9, (2006)). The RBCs that are loaded with the recombinant enzyme are then used for enzyme replacement therapy (ERT) by autologous blood. transfusion (i.e., collection followed by reinfusion of the patient's own RBCs). For example, RBCs that are loaded with recombinant human phenylalanine hydroxylase are given to a patient who suffers from phenylketouria (PKU) and lacks a functional PAH gene, which results in low levels of phenylalanine, hydroxylase. The RBC transfusion is performed adhering to previously described guidelines (see e.g. J. L. Carson et al., Red blood cell transfusion: a clinical practice guideline from the AABB, *Ann Intern Med*, 157(1): 49-58, (2012)). Since RBCs have an average life span in the human body of 120 days (D. Shemin and R. Rittenberg, The life span of the human red blood cell, *J Biol Chem.,* 166(2):627-36, (1946)), it is contemplated that the patient can receive a transfusion quarterly or biannually. Allogeneic blood transfusion (i.e., RBCs are collected from a matched donor) is performed following the same basic steps as described above. The recombinant protein can also be delivered into other non-adherent cell types, including but not limited to leukocytes, stem ells or other progenitor cells. These cells are purified following standard protocols known to a person skilled in the art.

To measure and optimize the intracellular delivery efficiency, GFP is used as the delivery agent and the percentage of GBP-positive RBCs is quantified with flow cytomety.

Example 4

Delivery of Mitochondria Into Oocytes.

Mitochondria are purified using standard protocols known to known to one skilled in the art, for example differential centrifugation and/or Nicoll gradient centrifugation (see e.g. J. M. Preble, et al., Rapid isolation and purification of mitochondria for transplantation by tissue dissociation and differential filtration, *J. Vis Exp.,* (91):51682, (2014)). Oocytes are obtained from sexually mature mice as described (see e.g. J. Van Blerkom, et al., Mitochondrial transfer between oocytes: potential applications of mitochondrial donation and the issue of heteroplasmy, *Hum Reprod.*, 13(1O):2857-68, (198)). The purified mitochondria and oocytes are pre-mixed (final concentration of mitochondria is about 1 mg/ml) and run through the MACS device to enable intracellular uptake of the mitochondria by the oocytes. To validate that the mitochondria are successfully taken up by the oocytes, the purified mitochondria are stained in vitro with Mitotracker Green FM (ThermoFisher Scientific), which localizes to mitochondria regardless of mitochondrial membrane potential, and the oocytes are imaged by fluorescence microscopy after they are collected from the outlet of the MACS device. Alternatively, DAPI (ThermoFisher Scientific) is used to strain the mitochondrial DNA (mtDNA) in vitro following a published protocol (M. Dellinger and M. Geze, Detection of mitochondrial DNA in living animal cells with fluorescence microscopy, 204(Pt 3):192-202, (2001)). Oocytes that are not incubated with labeled mitochondria are used as a negative control for the microscopy. It is known that mitochondrial transfer into oocytes from patients with repeated implantation failure after IVF treatment increases the clinical pregnancy rate (C. C. Huang, et al., Birth after the injection of sperm and the cytoplasm of tripronucleate zygotes into metaphase II oocytes in patients with repeated implantation failure after assisted fertilization procedures, *Fertil Steril*, 72(4):702-6, (1999)) but this process requires microinjection, which is labor intensive and low throughput.

Example 5

Loading Bacteria With a Payload for In Vivo Cancer Therapy.

Certain bacteria (e.g., *Salmonella, Escherichia coli, Clostridium, Listeria,* or *Bifidobacterium*) can grow inside tumors and even specifically accumulate within cancerous tissue upon systemic administration (c g., ingestion or intravenous injection), which makes these bacteria well-suited as delivery vehicles for cancer therapy (see e.g. M. Tangney, Gene therapy for cancer: dairy bacteria as delivery vectors. *Discov Med.*, (52): 195-200, (2010). However, loading bacteria with a small-molecule drug as a payload is challenging using existing methods. The MACS device is used to load a bacterium of interest with a small-molecule anti-cancer drug (e.g., doxorubicin or taxol) by briefly incubating the bacterial cells in the presence of high concentration (i.e., 10 µM to 1000 mM) of the small molecule, and then running the cell suspension through the MACS device to enable intracellular uptake Drug loading can be unproved by adding a compound to the growth medium that facilitates intracellular uptake (e.g., Pluronic F-68) and/or a bacterial efflux pump inhibitor (e.g., phenylalanine arginyl beta-naphthylamide) to prevent drug outflow. As a positive control for intracellular uptake, a cell-impermeable fluorescent dye like Alexa488 (ThermoFisher Scientific) is used and the amount of dye in the bacteria is quantified using fluorescence microscopy. To demonstrate that the drug-loaded bacteria localize to cancer cells in vivo and shrink tumors, a study with C57B6 mice bearing B16F10 melanomas is conducted as described (J. M. Pawelek, et al., Tumor-targeted *Salmonella* as a novel anticancer vector, *Cancer Res.,* 57(20):4537-44, (1997)). Bacteria that are not loaded with a drug or loaded with an inactive control compound are used as a negative control for the mouse study.

Example 6

Parallelize the MACS Device to Increase its Throughput for Intracellular Delivery.

To increase the throughput of the MACS device for intracellular delivery of an agent, a PMDS-based microfluidic chip that accommodates over 10,000 individual pressure-controlled MACS units that are all synchronously operated, is designed. The basic operating principle of the high throughput MACS dev ice is identical to the existing, standard MACS device (B. Okumus el al. Mechanical slowing-down of cytoplasmic diffusion allows in vivo counting of proteins in individual cells. *Nat Commun.,* 7:11641, (2016)). This parallel design greatly increases the throughput for intracellular delivery of an agent because a very larger number of cells are now compressed in parallel. This MACS device is operated as a stand-alone system, which does not require a microscope.

All publications cited herein expressly incorporated herein by reference in their entireties.

REFERENCES FOR EXAMPLE 1

(1) Tracy. B. P., Gaida. S. M & Papoutsakis, E. T. Flow cytometry for bacteria enabling metabolic engineering, synthetic biology and the elucidation of complex phenotypes. *Current Opinion in Biotechnology* 21, 85-99 (2010).
(2) Bongaerts, R. J., Hautefort, L, Sidebotham, J. M. & Hinton, J. C. Green fluorescent protein as a marker for conditional gene expression in bacterial cells. *Meth. Enzymol.* 358, 43-66 (2002).
(3) Felip, M., Andreatta, S., Sommaruga, R., Straskrábová, V. & Catalan, J. Suitability of flow cytometry for estimating bacterial biovolume in natural plankton samples: comparison with microscopy data. *Applied and Environmental Microbiology* 73, 4508-4514 (2007).
(4) Cisse, I. I. et al. Real-Time Dynamics of RNA Polymerase II Clustering in Live Human Cells, *Science* 341, 664-667 (2013).
(5) Okumus, B., Yildiz, S. & Toprak, E. Fluidic and microfluidic tools for quantitative systems biology. *Current Opinion in Biotechnology* (2014).
(6) Wang, P. et al. Robust Growth of *Escherichia coli*. *Current Biology,* 20, 1099-1103 (2010).
(7) Xie, X. S., Choi, P. J., Li, G.-W., Lee. N. K. & Lia, G. Single-Molecule Approach to Molecular Biology in Living Bacterial Cells. *Annu. Rev. Biophys.* 37, 417-444 (2008).
(8) Li, G.-W., Burkhardt, D., Gross, C. & Weissman, J. S. Quantifying absolute protein synthesis rates reveals principles underlying allocation of cellular resources. *CELL* 157, 624-635 (2014).
(9) Taniguchi, Y. et al. Quantifying *E. coli* proteome and transcriptome with single-molecule sensitivity in single cells. *Science* 329, 533-538 (2010).
(10) Uphoff, S. et at. Stochastic activation of a DNA damage response causes cell-to-cell mutation rate variation. *Science* 351, 1094-1097 (2016).
(11) Okumus, B. et al. Mechanical slowing-down of cytoplasmic diffusion allows in vivo counting of proteins in individual cells. *Nature Communications* 7, 11641 (2016).
(12) Unger, M. A. Monolithic Microfabricated Valves and Pumps by Multilayer Soft Lithography, *Science* 288, 113-116 (2000).
(13) Studer, V. Scaling properties of a low-actuation pressure microfluidic valve. 95, 393 (2004).
(14) Mazutis, L. et al. Single-cell analysis and sorting using droplet-based microfluidics. *Nat Protoc* 8, 870-891 (2013).
(15) Parry, B. R. et al. The Bacterial Cytoplasm Has Glasslike Properties and Is Fluidized by Metabolic Activity. *CELL* 156, 183-194 (2013).
(16) Elf, J., Li, G. W. & Xie, X. S. Probing Transcription Factor Dynamics at the Single-Molecule Level in a Living Cell. *Science* 316, 1191-1194 (2007).
(17) Veres, A. et al. Building a morbidostat: an automated continuous-culture device for studying bacterial drug resistance under dynamically sustained drug inhibition. *Nat Protoc* 8, 555-567 (2013).
(18) Frost, L. S. & Koraimann, G. Regulation of bacterial conjugation: balancing opportunity with adversity. *Future Microbiology* 5, 1057-1071 (2010).
(18) Lindqvist, R. C. & Nordstrom, K. Resistance of *Escherichia coli* to Penicillins VII. Purification and Characterization of a Penicillinase Mediated h the R Factor R1. *Journal of Bacteriology* (1970).

What is claimed is:
1. A method for uptake of an agent into a cell or population thereof using a microfluidic device, the method comprising:
    passing a first flow fluid through a flow channel of the microfluidic device, the flow channel being at least partially bounded on a first side by a flexible layer of the microfluidic device and being at least partially bounded on an opposing second side by a rigid layer of the microfluidic device, the first flow fluid including a plurality of a first type of cell therein and a first agent;
    pressurizing a control channel formed in the flexible layer of the microfluidic device such that the flexible layer physically compresses at least one of the first type of cell in the first flow fluid against the rigid layer to induce at least one temporary perturbation in a membrane of the at least one of the first type of cell; and
    causing a portion of the first agent to be taken up by the at least one of the first type of cell through the at least one temporary perturbation in the membrane of the at least one of the first type of cell.
2. The method of claim 1, wherein the causing the portion of the first agent to be taken up includes at least one of:
    continuing to pass the first flow fluid through the flow channel with the control channel pressurized;
    adjusting a flow rate of the first flow fluid through the flow channel with the control channel pressurized; or
    stopping the flow of the first flow fluid through the flow channel with the control channel pressurized.
3. The method of claim 1, wherein the agent is selected from the group consisting of: a DNA staining dye, a fluorescent molecule, a plasmid, a vector, a protein, a nucleic acid, a polypeptide, a recombinant RNA, an RNA, a siRNA, an shRNA, a miRNA, a compound, a small molecule, an antibody, a virus, a quantum dot (Qdot), a chromosome, a sequence encoding a chimeric antigen receptors (CAR) for CAR-modified T-cells (CAR-T), a drug, a therapeutic, an anti-sense oligonucleotide (ASO), an mRNA, an RNA aptamers, a protein aggregate, a protein fibril, a nanoparticle, a polysaccharide, a lipid, an organelle, a mitochondrion, a prokaryote, a microbial cell, and a bacterial cell.
4. The method of claim 1, wherein the fluid includes an extracellular growth factor.
5. The method of claim 1, wherein the cell is selected from the group consisting of: a prokaryote cell, a eukaryotic cell, a mammalian cell, a human cell, a microbial cell, a bacterial cell, a yeast cell, an artificial cells, a liposome, an oocyte, a red blood cell, a white blood cell, a cell having a generally rod shape with a diameter that is less than two micrometer and a length that is less than ten micrometers, a cell having a generally rod shape with a diameter that is between about 0.2 micrometers and about two micrometer, a cell having a generally biconcave shape with a diameter that is between about two micrometers and about twenty micrometers, and a cell having a diameter that is between about one micrometers and about twenty micrometers.
6. The method of claim 1, further comprising:
    passing a second flow fluid through the flow channel of the microfluidic device, the second flow fluid including a plurality of a second type of cell therein that is different from the first type of cell and a second agent;

pressurizing the control channel formed in the flexible layer of the microfluidic device such that the flexible layer physically compresses at least one of the second type of cell in the second flow fluid against the rigid layer to induce at least one temporary perturbation in a membrane of the at least one of the second type of cell; and causing a portion of the second agent to be taken up by the at least one of the second type of cell through the at least one temporary perturbation in the membrane of the at least one of the second type of cell.

7. The method of claim 1, wherein the second agent is the same or different as the first agent.

8. The method of claim 1, wherein the first type of cell is a prokaryotic cell and the second type of cell is a eukaryotic cell; or wherein the first type of cell and the second type of cell are a different prokaryotic cell; or wherein the first type of cell and the second type of cell are a different eukaryotic cell; or wherein the first type of cell and the second type of cell are a different diameter; or wherein the first type of cell and the second type of cell are a different shape.

9. A method of using a microfluidic device, the method comprising:

passing a first flow fluid through a flow channel of the microfluidic device, the flow channel being at least partially bounded on a first side by a flexible layer of the microfluidic device and being at least partially bounded on an opposing second side by a rigid layer of the microfluidic device, the first flow fluid including a plurality of a first type of cells therein and a first agent;

pressurizing, to a first pressure, a control channel formed in the flexible layer of the microfluidic device such that the flexible layer physically compresses at least one of the first type of cells in the first flow fluid against the rigid layer to induce at least one temporary perturbation in a membrane of the at least one of the first type of cell and permitting the at least one of the first type of cell to take up a portion of the first agent therethrough;

passing a second flow fluid through the flow channel of the microfluidic device, the second flow fluid including a plurality of a second type of cells therein that is different from the first type of cells and a second agent; and pressurizing, to a second pressure that is different from the first pressure, the control channel formed in the flexible layer of the microfluidic device such that the flexible layer physically compresses at least one of the second type of cells in the second flow fluid against the rigid layer to induce at least one temporary perturbation in a membrane of the at least one of the second type of cells and permitting the at least one of the second type of cells to take up a portion of the second agent therethrough.

10. The method of claim 9, wherein the first flow fluid is passed through the flow channel at a first time point.

11. The method of claim 9, wherein the second flow fluid is passed through the flow channel at a second time point.

12. The method of claim 9, wherein the second time point is a least 0.1 seconds following the first time point.

13. A method comprising:

a. passing a flow fluid through a flow channel of a microfluidic device, the flow channel being formed by a flexible layer and a cover layer, the flexible layer including a control channel therein that extends generally perpendicular to the flow channel, the fluid including an agent and a plurality of cells therein;

a. pressurizing the control channel;

b. forming a constriction in the flow channel;

c. physically compressing at least one of the plurality of cells in the fluid between the flexible layer and the cover layer at the formed constriction;

d. inducing at least one temporary perturbation in a membrane of the at least one of the plurality of cells; and e. causing the at least one of the plurality of cells to take up a portion of the agent through the at least one temporary perturbation of the membrane.

14. The method of claim 13, further comprising adjusting a flow rate of the flow fluid in the flow channel.

15. The method of claim 14, wherein the adjusting includes adjusting the flow rate of the flow fluid in the flow channel to zero flow.

16. The method of claim 15, wherein pressurizing the control channel causes the compression of the flow channel to occur, or causes the at least one of the plurality of cells to be physically compressed.

17. The method of claim 15, wherein the physical compression of the at least one of the plurality of cells induces at least one temporary perturbation in the membrane of the at least one of the plurality of cells.

18. The method of claim 15, wherein a pressure differential between a pressure inside the at least one of the plurality of cells and a pressure of the flowing fluid causes the at least one of the plurality of cells to take up the portion of the agent through the at least one temporary perturbation of the membrane.

19. The method of claim 15, wherein prior to the at least one of the plurality of cells being physically compressed, a pressure differential between a pressure inside the at least one of the plurality of cells and a pressure of the flowing fluid is insufficient to cause the at least one of the plurality of cells to take up the portion of the agent.

* * * * *